United States Patent
Rodrigues

(10) Patent No.: US 9,051,406 B2
(45) Date of Patent: Jun. 9, 2015

(54) GRAFT DENDRITE COPOLYMERS, AND METHODS FOR PRODUCING THE SAME

(71) Applicant: Akzo Nobel Chemicals International B.V., Amersfoort (NL)

(72) Inventor: Klin Aloysius Rodrigues, Signal Mountain, TN (US)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 0 days.

(21) Appl. No.: 14/355,319

(22) PCT Filed: Nov. 2, 2012

(86) PCT No.: PCT/EP2012/071742
§ 371 (c)(1),
(2) Date: Apr. 30, 2014

(87) PCT Pub. No.: WO2013/064648
PCT Pub. Date: May 10, 2013

(65) Prior Publication Data
US 2014/0309392 A1 Oct. 16, 2014

Related U.S. Application Data

(60) Provisional application No. 61/555,731, filed on Nov. 4, 2011, provisional application No. 61/555,750, filed on Nov. 4, 2011.

(30) Foreign Application Priority Data

Feb. 9, 2012 (EP) .................................... 12154684

(51) Int. Cl.
*C08F 251/00* (2006.01)
*A61Q 19/00* (2006.01)
(Continued)

(52) U.S. Cl.
CPC .................. *C08F 251/00* (2013.01); *A61Q 1/00* (2013.01); *A61Q 5/00* (2013.01); *A61Q 19/00* (2013.01);
(Continued)

(58) Field of Classification Search
USPC ................ 526/238.22; 525/54.2, 54.23, 54.3, 525/54.31; 527/313, 314
See application file for complete search history.

(56) References Cited

U.S. PATENT DOCUMENTS

| | | |
|---|---|---|
| 2,536,658 A | 1/1951 | Rheineck |
| 2,798,053 A | 7/1957 | Brown |

(Continued)

FOREIGN PATENT DOCUMENTS

| | | |
|---|---|---|
| CA | 2074747 | 2/1993 |
| CN | 1087649 A | 6/1994 |

(Continued)

OTHER PUBLICATIONS

Rosen, "Geminis: A new generation of surfactants," Chemtech, pp. 30-33 (Mar. 1993).

(Continued)

*Primary Examiner* — Vu A Nguyen
(74) *Attorney, Agent, or Firm* — Sandra B. Weiss

(57) ABSTRACT

Graft dendrite copolymers derived from at least one ethylenically unsaturated first monomer, at least one second ethylenically unsaturated second monomer and a natural hydroxyl containing component as an end group. The at least one first and second ethylenically unsaturated monomers are on separate side chains of the natural hydroxyl containing component. Methods of preparing a graft dendrite copolymer are also included.

18 Claims, 1 Drawing Sheet

(51) Int. Cl.
*A61K 8/91* (2006.01)
*B01J 20/26* (2006.01)
*A61Q 1/00* (2006.01)
*A61Q 5/00* (2006.01)
*C02F 1/56* (2006.01)
*C08F 220/06* (2006.01)
*C08F 220/58* (2006.01)
*C02F 11/14* (2006.01)
*C08F 2/00* (2006.01)

(52) U.S. Cl.
CPC ... *A61K 8/91* (2013.01); *C02F 1/56* (2013.01); *C08F 220/06* (2013.01); *A61K 2800/10* (2013.01); *A61K 2800/544* (2013.01); *C08F 2220/585* (2013.01); *C02F 11/14* (2013.01); *C08F 2/00* (2013.01); *B01J 20/261* (2013.01); *B01J 20/264* (2013.01); *B01J 2220/68* (2013.01)

(56) References Cited

U.S. PATENT DOCUMENTS

| | | |
|---|---|---|
| 2,954,347 A | 9/1960 | St. John et al. |
| 3,048,548 A | 8/1962 | Martin et al. |
| 3,308,067 A | 3/1967 | Diehl |
| 3,314,891 A | 4/1967 | Schmolka et al. |
| 3,334,147 A | 8/1967 | Brunelle et al. |
| 3,442,242 A | 5/1969 | Laskey et al. |
| 3,455,839 A | 7/1969 | Rauner |
| 3,518,176 A | 6/1970 | Reyes et al. |
| 3,629,121 A | 12/1971 | Eldib |
| 3,639,312 A | 2/1972 | Turner |
| 3,673,148 A | 6/1972 | Vasta |
| 3,687,878 A | 8/1972 | Imoto et al. |
| 3,723,322 A | 3/1973 | Diehl |
| 3,803,285 A | 4/1974 | Jensen |
| 3,929,107 A | 12/1975 | Renger |
| 3,929,678 A | 12/1975 | Laughlin et al. |
| 3,933,672 A | 1/1976 | Bartolotta et al. |
| 4,048,122 A | 9/1977 | Sibley et al. |
| 4,131,576 A | 12/1978 | Iovine et al. |
| 4,133,779 A | 1/1979 | Hellyer et al. |
| 4,141,841 A | 2/1979 | McDanald |
| 4,228,042 A | 10/1980 | Letton |
| 4,239,660 A | 12/1980 | Kingry |
| 4,260,529 A | 4/1981 | Letton |
| 4,265,779 A | 5/1981 | Gandolfo et al. |
| 4,322,472 A | 3/1982 | Kaspar et al. |
| 4,374,035 A | 2/1983 | Bossu |
| 4,379,080 A | 4/1983 | Murphy |
| 4,388,205 A | 6/1983 | Stettler et al. |
| 4,412,934 A | 11/1983 | Chung et al. |
| 4,483,779 A | 11/1984 | Llenado et al. |
| 4,483,780 A | 11/1984 | Llenado |
| 4,536,314 A | 8/1985 | Hardy et al. |
| 4,539,130 A | 9/1985 | Thompson et al. |
| 4,557,763 A | 12/1985 | George et al. |
| 4,565,647 A | 1/1986 | Llenado |
| 4,597,898 A | 7/1986 | Vander Meer |
| 4,605,721 A | 8/1986 | Jenkins et al. |
| 4,606,838 A | 8/1986 | Burns |
| 4,618,914 A | 10/1986 | Sato et al. |
| 4,634,551 A | 1/1987 | Burns et al. |
| 4,652,392 A | 3/1987 | Baginski et al. |
| 4,671,891 A | 6/1987 | Hartman |
| 4,681,592 A | 7/1987 | Hardy et al. |
| 4,681,695 A | 7/1987 | Divo |
| 4,681,704 A | 7/1987 | Bernardino et al. |
| 4,686,063 A | 8/1987 | Burns |
| 4,702,857 A | 10/1987 | Gosselink |
| 4,782,901 A | 11/1988 | Phelps et al. |
| 4,830,773 A | 5/1989 | Olson |
| 4,855,069 A | 8/1989 | Schuppiser et al. |
| 4,963,629 A | 10/1990 | Driemel et al. |
| 4,968,451 A | 11/1990 | Scheibel et al. |
| 5,032,659 A * | 7/1991 | Heidel .................. 527/300 |
| 5,071,895 A | 12/1991 | Hughes et al. |
| 5,076,968 A | 12/1991 | Fringeli et al. |
| 5,121,795 A | 6/1992 | Ewert et al. |
| 5,125,455 A | 6/1992 | Harris et al. |
| 5,223,171 A | 6/1993 | Jost et al. |
| 5,227,446 A | 7/1993 | Denzinger et al. |
| 5,248,449 A | 9/1993 | Mitchell et al. |
| 5,264,470 A | 11/1993 | Eoff |
| 5,296,470 A | 3/1994 | Vaslin et al. |
| 5,304,620 A | 4/1994 | Holtmyer et al. |
| 5,326,864 A | 7/1994 | Besemer et al. |
| 5,332,528 A | 7/1994 | Pan et al. |
| 5,378,830 A | 1/1995 | Yeh |
| 5,385,959 A | 1/1995 | Tsaur et al. |
| 5,412,026 A | 5/1995 | Holy et al. |
| 5,415,807 A | 5/1995 | Gosselink et al. |
| 5,435,935 A | 7/1995 | Kupneski |
| 5,478,503 A | 12/1995 | Swift |
| 5,500,154 A | 3/1996 | Bacon et al. |
| 5,501,815 A | 3/1996 | Man |
| 5,518,646 A | 5/1996 | Van den Brom |
| 5,518,657 A | 5/1996 | Fringeli et al. |
| 5,523,023 A | 6/1996 | Kleinstuck et al. |
| 5,543,459 A | 8/1996 | Hartmann et al. |
| 5,547,612 A | 8/1996 | Austin et al. |
| 5,565,145 A | 10/1996 | Watson et al. |
| 5,580,154 A | 12/1996 | Coulter et al. |
| 5,580,941 A | 12/1996 | Krause et al. |
| 5,583,193 A | 12/1996 | Aravindakshan et al. |
| 5,654,198 A | 8/1997 | Carrier et al. |
| 5,656,646 A | 8/1997 | Perner et al. |
| 5,658,651 A | 8/1997 | Smith et al. |
| 5,670,475 A | 9/1997 | Trinh et al. |
| 5,674,511 A | 10/1997 | Kacher et al. |
| 5,753,770 A | 5/1998 | Breitenbach et al. |
| 5,756,442 A | 5/1998 | Jeschke et al. |
| 5,760,154 A | 6/1998 | Krause et al. |
| 5,830,241 A | 11/1998 | Rohringer et al. |
| 5,852,069 A | 12/1998 | Meister et al. |
| 5,854,191 A | 12/1998 | Krause et al. |
| 5,854,321 A | 12/1998 | Krause et al. |
| 5,869,070 A | 2/1999 | Dixon et al. |
| 5,942,477 A | 8/1999 | Giret et al. |
| 5,942,479 A | 8/1999 | Frankenbach et al. |
| 5,942,485 A | 8/1999 | Kemen |
| 5,945,127 A | 8/1999 | Breitenbach et al. |
| 5,952,278 A | 9/1999 | Mao et al. |
| 5,977,275 A | 11/1999 | Rodrigues et al. |
| 5,985,809 A | 11/1999 | Frankenbach et al. |
| 5,990,065 A | 11/1999 | Vinson et al. |
| 6,004,922 A | 12/1999 | Watson et al. |
| 6,008,181 A | 12/1999 | Cripe et al. |
| 6,020,303 A | 2/2000 | Cripe et al. |
| 6,022,844 A | 2/2000 | Baillely et al. |
| 6,025,311 A | 2/2000 | Clarke et al. |
| 6,060,299 A | 5/2000 | Sreekrishna et al. |
| 6,060,443 A | 5/2000 | Cripe et al. |
| 6,060,582 A | 5/2000 | Hubbell et al. |
| 6,069,122 A | 5/2000 | Vinson et al. |
| 6,093,856 A | 7/2000 | Cripe et al. |
| 6,103,839 A | 8/2000 | Patel et al. |
| 6,106,849 A | 8/2000 | Malkan et al. |
| 6,130,194 A | 10/2000 | Pancheri et al. |
| 6,136,769 A | 10/2000 | Asano et al. |
| 6,143,707 A | 11/2000 | Trinh et al. |
| 6,150,322 A | 11/2000 | Singleton et al. |
| 6,153,570 A | 11/2000 | Decoster |
| 6,153,577 A | 11/2000 | Cripe et al. |
| 6,162,423 A | 12/2000 | Sebag et al. |
| 6,169,062 B1 | 1/2001 | Salager et al. |
| 6,194,362 B1 | 2/2001 | Trinh et al. |
| 6,221,825 B1 | 4/2001 | Williams, Jr. et al. |
| 6,225,462 B1 | 5/2001 | Berry et al. |
| 6,231,650 B1 | 5/2001 | Mallow et al. |
| 6,255,427 B1 | 7/2001 | Exner et al. |
| 6,303,560 B1 | 10/2001 | Hartan et al. |
| 6,365,561 B1 | 4/2002 | Vinson et al. |

(56) References Cited

U.S. PATENT DOCUMENTS

| | | |
|---|---|---|
| 6,372,708 B1 | 4/2002 | Kasturi et al. |
| 6,376,438 B1 | 4/2002 | Rosenberger et al. |
| 6,384,132 B1 | 5/2002 | Horley et al. |
| 6,423,775 B1 | 7/2002 | Brune et al. |
| 6,451,747 B1 | 9/2002 | Decoster |
| 6,482,994 B2 | 11/2002 | Scheper et al. |
| 6,528,477 B2 | 3/2003 | Kasturi et al. |
| 6,537,957 B1 | 3/2003 | Cardola et al. |
| 6,573,234 B1 | 6/2003 | Sivik et al. |
| 6,589,926 B1 | 7/2003 | Vinson et al. |
| 6,605,182 B1 | 8/2003 | Danner |
| 6,627,590 B1 | 9/2003 | Sherry et al. |
| 6,645,925 B2 | 11/2003 | Sivik et al. |
| 6,656,900 B2 | 12/2003 | Sivik et al. |
| 6,764,992 B2 | 7/2004 | Kumar et al. |
| 6,800,712 B2 | 10/2004 | Doane et al. |
| 6,867,262 B1 | 3/2005 | Angel et al. |
| 6,908,955 B2 | 6/2005 | Porsch et al. |
| 6,911,053 B1 | 6/2005 | Bijsterbosch et al. |
| 7,012,048 B2 | 3/2006 | Drovetskaya et al. |
| 7,087,662 B2 | 8/2006 | Ghosh et al. |
| 7,151,079 B2 | 12/2006 | Fack et al. |
| 7,153,821 B2 | 12/2006 | Blokzijl et al. |
| 7,157,413 B2 | 1/2007 | Lazzeri et al. |
| 7,435,293 B2 | 10/2008 | Caveny et al. |
| 7,589,051 B2 | 9/2009 | Erazo-Majewicz et al. |
| 7,666,963 B2 | 2/2010 | Rodrigues et al. |
| 7,670,388 B2 | 3/2010 | Sugano et al. |
| 7,727,945 B2 | 6/2010 | Rodrigues et al. |
| 7,740,873 B2 | 6/2010 | Decoster et al. |
| 7,754,666 B2 | 7/2010 | Walters et al. |
| 7,902,276 B2 | 3/2011 | Sakai et al. |
| 2002/0016282 A1 | 2/2002 | Kumar et al. |
| 2002/0034487 A1 | 3/2002 | Maubru et al. |
| 2002/0055446 A1 | 5/2002 | Perron et al. |
| 2002/0106747 A1 | 8/2002 | Cheng et al. |
| 2002/0173592 A1 | 11/2002 | Saeki et al. |
| 2003/0008793 A1 | 1/2003 | Takiguchi et al. |
| 2003/0008804 A1 | 1/2003 | Xu et al. |
| 2003/0092584 A1 | 5/2003 | Crews |
| 2003/0147827 A1 | 8/2003 | Decoster et al. |
| 2003/0147842 A1 | 8/2003 | Restle et al. |
| 2003/0211952 A1 | 11/2003 | Erazo Majewicz et al. |
| 2004/0033929 A1 | 2/2004 | Bertleff et al. |
| 2004/0039137 A1 | 2/2004 | Heinemann et al. |
| 2004/0048760 A1 | 3/2004 | Rabon et al. |
| 2004/0067864 A1 | 4/2004 | Aubay et al. |
| 2004/0067865 A1 | 4/2004 | Harrison |
| 2004/0071742 A1 | 4/2004 | Popplewell et al. |
| 2004/0092425 A1 | 5/2004 | Boutique et al. |
| 2004/0102354 A1 | 5/2004 | Fack et al. |
| 2004/0103483 A1 | 6/2004 | Delplancke et al. |
| 2004/0107505 A1 | 6/2004 | Harrison et al. |
| 2004/0147425 A1 | 7/2004 | Castro et al. |
| 2004/0170596 A1 | 9/2004 | Hauschel et al. |
| 2004/0214736 A1 | 10/2004 | Modi |
| 2004/0266653 A1 | 12/2004 | Delplancke et al. |
| 2004/0266655 A1 | 12/2004 | Baum et al. |
| 2005/0019352 A1 | 1/2005 | Mercier et al. |
| 2005/0028293 A1 | 2/2005 | Geffroy |
| 2005/0108832 A1 | 5/2005 | Torri et al. |
| 2005/0143278 A1 | 6/2005 | Pegelow et al. |
| 2005/0171287 A1 | 8/2005 | Baum et al. |
| 2005/0175572 A1 | 8/2005 | Nguyen-Kim et al. |
| 2005/0176878 A1 | 8/2005 | Ettl et al. |
| 2005/0202985 A1 | 9/2005 | Nieendick et al. |
| 2005/0202989 A1 | 9/2005 | Wilson |
| 2005/0215449 A1 | 9/2005 | Penninger et al. |
| 2005/0256027 A1 | 11/2005 | Heibel et al. |
| 2005/0267008 A1 | 12/2005 | Carvell et al. |
| 2005/0271595 A1 | 12/2005 | Brown |
| 2005/0276831 A1 | 12/2005 | Dihora et al. |
| 2006/0019847 A1 | 1/2006 | Fan et al. |
| 2006/0019858 A1 | 1/2006 | Kruse et al. |
| 2006/0024353 A1 | 2/2006 | Trouve et al. |
| 2006/0029561 A1 | 2/2006 | Gunn et al. |
| 2006/0106186 A1 | 5/2006 | Dupont et al. |
| 2006/0111511 A1 | 5/2006 | Narayan et al. |
| 2006/0182917 A1 | 8/2006 | Wood et al. |
| 2006/0183203 A1 | 8/2006 | DeAngelis |
| 2006/0183856 A1 | 8/2006 | Wood et al. |
| 2006/0183857 A1 | 8/2006 | Wood et al. |
| 2006/0252901 A1 | 11/2006 | Narayan et al. |
| 2006/0258555 A1 | 11/2006 | Filippini et al. |
| 2006/0258557 A1 | 11/2006 | Popplewell et al. |
| 2006/0281654 A1 | 12/2006 | Brooker et al. |
| 2007/0015678 A1 | 1/2007 | Rodrigues et al. |
| 2007/0021577 A1 | 1/2007 | Rodrigues et al. |
| 2007/0054816 A1 | 3/2007 | Berthier et al. |
| 2007/0056900 A1 | 3/2007 | Mathauer et al. |
| 2007/0111920 A1 | 5/2007 | Baur et al. |
| 2007/0138105 A1 | 6/2007 | Takeda et al. |
| 2007/0260046 A1 | 11/2007 | Tomita et al. |
| 2008/0020948 A1 | 1/2008 | Rodrigues et al. |
| 2008/0020961 A1* | 1/2008 | Rodrigues et al. ............ 510/475 |
| 2008/0021167 A1 | 1/2008 | Rodrigues |
| 2008/0021168 A1 | 1/2008 | Rodrigues et al. |
| 2008/0118568 A1 | 5/2008 | Smets et al. |
| 2008/0139441 A1 | 6/2008 | Xiao et al. |
| 2008/0146478 A1 | 6/2008 | Lei et al. |
| 2008/0230193 A1 | 9/2008 | Mori et al. |
| 2008/0274940 A1 | 11/2008 | Tjelta et al. |
| 2008/0274942 A1 | 11/2008 | Tjelta et al. |
| 2008/0277620 A1 | 11/2008 | Kesavan et al. |
| 2008/0305982 A1 | 12/2008 | Smets et al. |
| 2008/0311064 A1 | 12/2008 | Lei et al. |
| 2009/0011214 A1 | 1/2009 | Wang |
| 2009/0011973 A1 | 1/2009 | Besse et al. |
| 2009/0023625 A1 | 1/2009 | Tang et al. |
| 2009/0062175 A1 | 3/2009 | Cermenati et al. |
| 2009/0087390 A1 | 4/2009 | Modi |
| 2009/0176687 A1 | 7/2009 | Tjelta et al. |
| 2009/0258042 A1 | 10/2009 | Anastasiou et al. |
| 2009/0258810 A1 | 10/2009 | Song et al. |
| 2009/0326165 A1 | 12/2009 | Patil et al. |
| 2010/0008870 A1 | 1/2010 | Dihora et al. |
| 2010/0056413 A1 | 3/2010 | Harry, Jr. et al. |
| 2010/0069280 A1 | 3/2010 | Rodrigues et al. |
| 2010/0075879 A1 | 3/2010 | Gizaw et al. |
| 2010/0075880 A1 | 3/2010 | Dupont et al. |
| 2010/0075887 A1 | 3/2010 | Wang et al. |
| 2010/0086575 A1 | 4/2010 | Dihora et al. |
| 2010/0093584 A1 | 4/2010 | Brand et al. |
| 2010/0154831 A1 | 6/2010 | Neplenbrock et al. |
| 2010/0167547 A1 | 7/2010 | Kamimura |
| 2010/0236736 A1 | 9/2010 | Brockmeyer et al. |
| 2010/0280146 A1 | 11/2010 | Vanderlaan et al. |
| 2010/0317560 A1 | 12/2010 | Ryther et al. |
| 2011/0017945 A1 | 1/2011 | Miralles et al. |
| 2011/0021410 A1 | 1/2011 | Miralles et al. |
| 2011/0028371 A1 | 2/2011 | Rodrigues et al. |
| 2011/0034622 A1 | 2/2011 | Kawamura et al. |
| 2011/0118168 A1 | 5/2011 | Schunicht et al. |
| 2011/0136718 A1 | 6/2011 | Rodrigues et al. |
| 2013/0035273 A1 | 2/2013 | Silvernail et al. |
| 2013/0035274 A1 | 2/2013 | Silvernail et al. |
| 2013/0035275 A1 | 2/2013 | Silvernail et al. |
| 2013/0035276 A1 | 2/2013 | Silvernail et al. |
| 2013/0035277 A1 | 2/2013 | Silvernail et al. |

FOREIGN PATENT DOCUMENTS

| | | |
|---|---|---|
| CN | 101830015 A | 9/2010 |
| CN | 101863540 A | 10/2010 |
| CN | 102146150 A | 8/2011 |
| DE | 40 38 908 A1 | 6/1992 |
| EP | 0 130 756 A1 | 1/1985 |
| EP | 0 404 377 A1 | 12/1990 |
| EP | 0 405 917 A1 | 1/1991 |
| EP | 00438215 | 1/1991 |
| EP | 0 441 197 A2 | 8/1991 |
| EP | 0 526 800 A1 | 2/1993 |
| EP | 0 577 519 A1 | 1/1994 |
| EP | 0 605 084 A1 | 7/1994 |

(56) References Cited

FOREIGN PATENT DOCUMENTS

| | | |
|---|---|---|
| EP | 0505371 B1 | 3/1996 |
| EP | 0 725 131 A1 | 8/1996 |
| EP | 0725131 A1 | 8/1996 |
| EP | 0526800 B1 | 1/1997 |
| EP | 0 869 169 A1 | 10/1998 |
| EP | 0653485 B1 | 5/2000 |
| EP | 1 007 529 B1 | 6/2000 |
| EP | 1 022 294 B1 | 7/2000 |
| EP | 1021156 B1 | 7/2000 |
| EP | 1043388 B1 | 10/2000 |
| EP | 1043389 B1 | 10/2000 |
| EP | 0703243 B1 | 12/2000 |
| EP | 0628655 B1 | 5/2001 |
| EP | 1 236 748 A1 | 9/2002 |
| EP | 1506765 B1 | 2/2005 |
| EP | 1162257 B1 | 2/2006 |
| EP | 1520004 B1 | 12/2006 |
| EP | 1 881 017 A2 | 1/2008 |
| EP | 1997874 A1 | 3/2008 |
| EP | 1950232 A1 | 7/2008 |
| EP | 1699429 B1 | 10/2008 |
| EP | 2014757 A1 | 1/2009 |
| EP | 1741775 B1 | 4/2009 |
| EP | 2 072 531 A1 | 6/2009 |
| EP | 2 138 560 B1 | 12/2009 |
| EP | 1877171 B1 | 3/2010 |
| FR | 2856073 A1 | 12/2004 |
| FR | 2 908 135 A1 | 5/2008 |
| FR | 2 927 083 A1 | 8/2009 |
| GB | 1137741 | 12/1968 |
| GB | 1322536 A | 7/1973 |
| GB | 1355998 A | 6/1974 |
| GB | 1464616 A | 2/1977 |
| GB | 2322137 A | 8/1998 |
| GB | 2432844 A | 6/2007 |
| GB | 2432852 A | 6/2007 |
| JP | 57-082145 | 5/1982 |
| JP | 6157253 | 6/1994 |
| JP | 6-298866 | 10/1994 |
| JP | 6-315622 | 11/1994 |
| JP | 9249892 | 9/1997 |
| JP | 11-343449 | 12/1999 |
| JP | 2000017299 | 1/2000 |
| JP | 2002-526611 | 8/2002 |
| JP | 2002285019 | 10/2002 |
| JP | 2004-107233 | 4/2004 |
| JP | 2005-120045 | 5/2005 |
| JP | 2005-532304 | 10/2005 |
| JP | 2008208051 | 9/2008 |
| JP | 2010-47713 | 3/2010 |
| JP | 2011-195809 | 10/2011 |
| WO | WO 91/06637 | 5/1991 |
| WO | WO 92/06162 | 4/1992 |
| WO | WO 92/10433 | 6/1992 |
| WO | WO 93/02118 | 2/1993 |
| WO | WO 93/11214 | 6/1993 |
| WO | WO 93/19038 | 9/1993 |
| WO | WO 93/19146 | 9/1993 |
| WO | WO 94/09099 | 4/1994 |
| WO | WO 95/10591 | 4/1995 |
| WO | WO 95/26393 | 10/1995 |
| WO | WO 95/26710 A1 | 10/1995 |
| WO | WO 96/35645 A1 | 11/1996 |
| WO | WO 96/37503 A1 | 11/1996 |
| WO | WO 97/45510 A1 | 12/1997 |
| WO | WO 98/18352 A1 | 5/1998 |
| WO | WO 98/35002 | 8/1998 |
| WO | WO 98/35003 | 8/1998 |
| WO | WO 98/35004 | 8/1998 |
| WO | WO 98/35005 | 8/1998 |
| WO | WO 98/35006 | 8/1998 |
| WO | WO 98/49260 A1 | 11/1998 |
| WO | WO 99/02663 | 1/1999 |
| WO | WO 99/05082 | 2/1999 |
| WO | WO 99/05084 | 2/1999 |
| WO | WO 99/05241 | 2/1999 |
| WO | WO 99/05242 | 2/1999 |
| WO | WO 99/05243 | 2/1999 |
| WO | WO 99/05244 | 2/1999 |
| WO | WO 99/07656 | 2/1999 |
| WO | WO 99/20726 | 4/1999 |
| WO | WO 99/27083 | 6/1999 |
| WO | WO 99/36470 A1 | 7/1999 |
| WO | WO 00/12661 A1 | 3/2000 |
| WO | WO 00/15180 A1 | 3/2000 |
| WO | WO 00/18868 A1 | 4/2000 |
| WO | WO 00/20470 | 4/2000 |
| WO | WO 00/23548 | 4/2000 |
| WO | WO 00/23549 | 4/2000 |
| WO | WO 00/36076 A1 | 6/2000 |
| WO | WO 00/47708 | 8/2000 |
| WO | WO 01/24779 A1 | 4/2001 |
| WO | WO 01/32816 A1 | 5/2001 |
| WO | WO 01/42408 A2 | 6/2001 |
| WO | WO 02/38715 A2 | 5/2002 |
| WO | WO 02/44686 A2 | 6/2002 |
| WO | WO 03/042262 A2 | 5/2003 |
| WO | WO 03/095597 A1 | 11/2003 |
| WO | WO 2004/046301 A1 | 6/2004 |
| WO | WO 2004/048418 A2 | 6/2004 |
| WO | WO 2005/012378 A1 | 2/2005 |
| WO | WO 2005/051343 A1 | 6/2005 |
| WO | WO 2005/059023 A1 | 6/2005 |
| WO | WO 2006/002565 A1 | 1/2006 |
| WO | WO 2006/007945 A1 | 1/2006 |
| WO | WO 2006/026406 A2 | 3/2006 |
| WO | WO 2006/119162 A1 | 11/2006 |
| WO | WO 2007/140267 A1 | 12/2007 |
| WO | WO 2008/089262 A1 | 7/2008 |
| WO | WO 2008/144744 A2 | 11/2008 |
| WO | WO 2008/147940 A2 | 12/2008 |
| WO | WO 2009/006603 A1 | 1/2009 |
| WO | WO 2009/087525 A1 | 7/2009 |
| WO | WO 2009/156233 A1 | 12/2009 |
| WO | WO 2010/057977 A1 | 5/2010 |
| WO | WO 2010/065482 A1 | 6/2010 |
| WO | WO 2010/065483 A1 | 6/2010 |
| WO | WO 2010/079466 A2 | 7/2010 |
| WO | WO 2010/079467 A2 | 7/2010 |
| WO | WO 2011/014783 A1 | 2/2011 |
| WO | WO 2011/017223 A1 | 2/2011 |
| WO | WO 2011/025624 A1 | 3/2011 |
| WO | WO 2012/000609 A1 | 1/2012 |

OTHER PUBLICATIONS

"Gemini Surfactants: A New Class of Self-Assembling Molecules," J. American Chemical Soc., vol. 115, pp. 10083-10090 (1993).

Kirk Othmer Encyclopedia of Chemical Technology, 3rd Ed, vol. 7, pp. 430-447 (John Wiley & Sons, Inc., 1979).

Kroschwitz, J.I.; Concise Encyclopedia of Polymer Science & Engineering, Ed., Wiley-Interscience, New York, p. 436 (1990).

Mark, Herman F., Concise Encyclopedia of Polymer Science and Technology, 3rd Ed., vol. 11, Wiley-Interscience, New York, p. 380 (2004).

Odian, George; Principles of Polymerization, 2nd Ed., Wiley-Interscience, New York, p. 424 (1970).

Odian, Principles of Polymerization, 2nd Ed., John Wiley & Sons, p. 226, New York (1981).

Wurzburg, Modified Starches: Properties and Uses, Grafted Starches, Chpt. 10, pp. 149-172, CRC Press, Boca Raton (1986).

Dubois et al, "Colorimetric Method for Determination of Sugars and Related Substances," Analytical Chemistry, vol. 28, No. 3, pp. 350-356 ( Mar. 1956).

Kwei-Ping, et al, "Chain Transfer constant of Vinylpyrrolidone with Dextran," Institute of Polymer Research, vol. 66, pp. 828-829, May 1962.

European Search Report for EP Application No. 06015025.7; Nov. 13, 2006.

European Search Report for EP Application No. 07014413.4; Nov. 6, 2007.

(56) References Cited

OTHER PUBLICATIONS

European Search Report for EP Application No. 07014412.6; Oct. 18, 2007.
European Search Report for EP Application No. 07014412.6; Jan. 23, 2008.
European Search Report for EP Application No. 09175465.5; Jan. 14, 2010.
Questel QPatents Abstract for Japanese Patent Publication 11-343449.
Chinese Office Action Action mailed Jul. 1, 2010 for Patent Application No. 200710169190.X.
International Search Report for PCT Application No. US2010/043919; Completed Sep. 22, 2010.
International Search Report for PCT Application No. US2010/043930; Completed Sep. 23, 2010.
International Search Report and Written Opinion for Application No. PCTEP2011/073928; Completion Date Jan. 18, 2012.
European Search Report for Application No. 11158599.8; Completion Date Aug. 11, 2011.
Shen, et al, "Graft Copolymers of Vinyl Pyrrolidone on Dextran," Journal of Polymer Science, vol. 53, pp. 81-85 (1961).
Kahya, et al, "A Novel Copolymer: Starch-g-Polyvinylpyrrolidone," Starch/Starke 61 (2009), pp. 267-274.
English QPatent Abstract for European Patent Publication No. 0 577 519 A1.
English Abstract for Japanese Patent Publication No. JP 2005/120045 (Abstract No. 2005-359217/37).
European Search Report for Application No. 12154675.8; Completion Date May 14, 2012.
European Search Report for Application No. 12154684.0; Completion Date May 14, 2012.
English Abstract for Japanese Patent Publication No. JP 57-082145.
English Translation of Japanese Office Action mailed Jun. 5, 2012; (Application No. 2006-198098).
English Abstract of Chinese Publication No. CN 101830015 A.
English Abstract of Chinese Publication No. CN 101863540 A.
English Abstract of Chinese Publication No. CN 102146150 A.
English Translation of European Publication No. EP 0 725 131 A1.
English Translation of European Publication No. EP 2 072 531 A1.
English Translation of French Publication No. FR 2 908 135 A1.
English Translation of French Publication No. FR 2 927 083 A1.
English Abstract of Japanese Publication No. JP 6-298866 A.
English Abstract of Japanese Publication No. JP 2010-47713 A.
English Abstract of Japanese Publication No. JP 2011-195809 A.
International Search Report issued in PCT/US2012/049514 mailed Feb. 19, 2013, 3 pages.
International Search Report and Written Opinion issued in PCT/US2012/049595, mailed Feb. 25, 2013, 10 pages.
International Search Report and Written Opinion issued in International Application No. PCT/US2012/049547, mailed Jan. 23, 2013, 11 pages.
International Search Report and Written Opinion issued in PCT/US2012/049564, mailed Jan. 23, 2013,10 pages.
International Search Report and Written Opinion issued in PCT/US2012/049584, mailed Jan. 21, 2013, 11 pages.
Athawale et al., "Graft Polymerization: Starch as a Model Substrate", J.M.S. Rev. Macromol. Chem. Phys., C39(3), 445-480, 1999.
Willett et al., "Initiator Effects in Reactive Extrusion of Starch-Polyacrylamide Graft Copolymers," Wiley InterScience, Received May 28, 2004; Accepted Feb. 22, 2005, pp. 52-58.
Water PurificationHandbook, Ch 25, Deposit and Scale Control-Cooling System, retrieved from: http://www.gewater.com/handbook/cooling_water_system.ch_25_deposit.jsp © 1997-2012.
English Abstract for European Publication No. 0628655 A1.
English Abstract for European Publication No. 0725131 A1.
French Publication 2768616—English Translation for European Publication No. 1021156 B1.
English Abstract for European Publication No. 1043388 A1.
English Abstract for European Publication No. 1043389 A1.
English Abstract for European Publication No. 1506765 A1.
English Abstract for European Publication No. 1520004 A1.
English Abstract for European Publication No. 1699429 A1.
English Translation for European Publication No. 1877171 A1.
English Abstract for French Publication No. 2856073 A1.
English Abstract for Japanese Publication No. 2000017299 A1.
English Abstract for Japanese Publication No. 2002285019 A1.
English Abstract for Japanese Publication No. 2008208051 A1.
English Abstract for Japanese Publication No. 6157253 A1.
English Abstract for Japanese Publication No. 6298866 A1.
English Abstract for Japanese Publication No. 9249892 A1.
EnglishTranslation of Japanese Office Action mailed Oct. 22, 2013 for Application No. 2012-523097.
English Abstract of Japanese Publication No. 2004-107233.

* cited by examiner

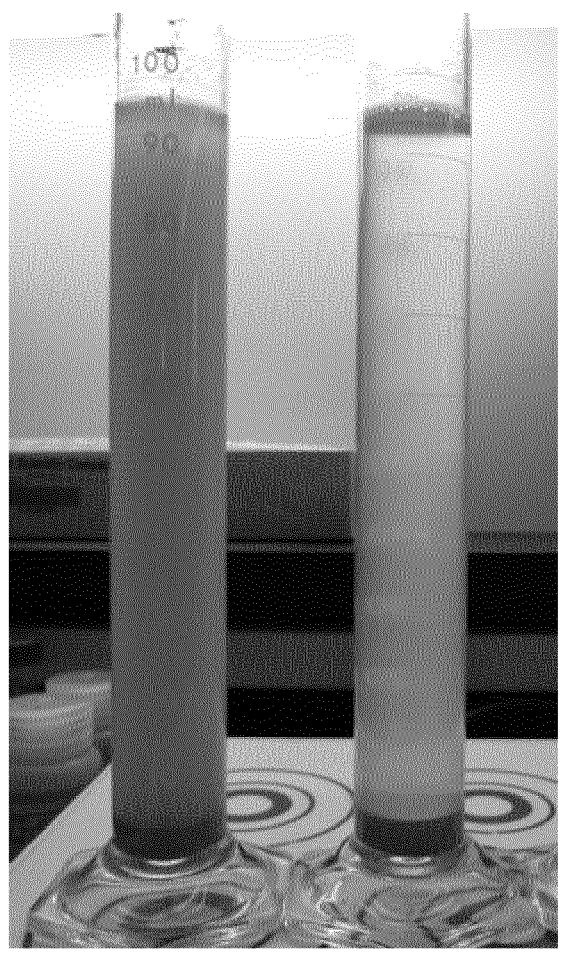

GRAFT DENDRITE COPOLYMERS, AND METHODS FOR PRODUCING THE SAME

This application is a National Phase Application of PCT Application No. PCT/EP2012/071742, filed Nov. 2, 2012, and claims the benefit of priority to U.S. Provisional Patent Application Nos. 61/555,731 and 61/555,750 each filed Nov. 4, 2011 and EP Application No. 12154684.0, filed Feb. 9, 2012. Each of these applications is hereby incorporated by reference in its entirety herein.

FIELD OF THE INVENTION

The present invention is relates to graft dendrite copolymers which contain a portion of a naturally occurring oligomer or polymer and a moiety from at least two synthetically derived oligomers or polymers.

BACKGROUND

A number of attempts have been made in the past to use natural materials as polymeric building blocks. These have mainly centered on grafting natural materials (e.g., sugars and starches) with synthetic monomers. For example, U.S. Pat. Nos. 5,854,191, 5,223,171, 5,227,446 and 5,296,470 disclose the use of graft copolymers in cleaning applications. U.S. Pat. Nos. 5,580,154 and 5,580,941 disclose sulfonated monomers grafted onto mono-, di- and oligosaccharides.

The synthetic portions of these graft copolymers disclosed in the literature are made up of mixtures of the synthetic monomers if more than one monomer is used. This leads to the formation of synthetic chains in the graft copolymer that have a blend of properties of the two monomers which does not take full advantage of the functionality of both monomer moieties.

Accordingly, there is a need to maximize the performance obtained from these monomers.

SUMMARY OF THE INVENTION

In view of the problems noted above, generally, graft dendrite copolymers can be synthesized where each synthetic chain contains only one of the monomers. This can be achieved by adding the two distinct monomers sequentially so that the monomers do not react with each other while forming the synthetic portion of these graft dendrite copolymers. Graft dendrite copolymers derived therefrom contain a portion of a naturally occurring oligomer or polymer and a moiety from each of the synthetically derived oligomers or polymers and attached at different points on the natural polymer. In an aspect, the invention therefore provides a graft dendrite copolymer comprising at least one first ethylenically unsaturated monomer, at least one second ethylenically unsaturated monomer, that is different from the first ethylenically unsaturated monomer, and at least one natural hydroxyl containing component. The at least one first and the at least one second ethylenically unsaturated monomers are attached at different points on the natural hydroxyl containing component.

In another aspect, the invention is directed to graft dendrite copolymers obtained by polymerization of at least one first one ethylenically unsaturated monomer and at least one second ethylenically unsaturated monomer in the presence of a natural hydroxyl containing component wherein the monomers are polymerized sequentially and the polymerization is metal ion catalyst initiated.

BRIEF DESCRIPTION OF THE DRAWING

The invention is best understood from the following detailed description when read in connection with the accompanying drawings. Included in the drawings is the following FIGURE:

The FIGURE is a photograph showing the results of a dispersancy test comparing a polymer solution prepared in accordance with the present invention to a conventional polymer solution as prepared in Comparative Example 1.

DETAILED DESCRIPTION OF THE INVENTION

Generally, the graft dendrite copolymers of the instant invention are formed by preparing graft dendrite copolymers in which two or more synthetic polymer chains of two or more distinct synthetic monomers are polymerized in the presence of a natural hydroxyl containing component wherein the polymerization of the two or more distinct synthetic monomers occurs sequentially. The resulting graft dendrite copolymers have one synthetic chain from one monomer, such as acrylic acid, and the second synthetic chain from another monomer, such as a 2-acrylamido-2-methyl propane sulfonic acid, wherein the two chains are attached to the natural hydroxyl containing component at separate and distinct points. It is preferably that the separate and distinct points be on the same molecule of the natural hydroxyl containing component as illustrated below.

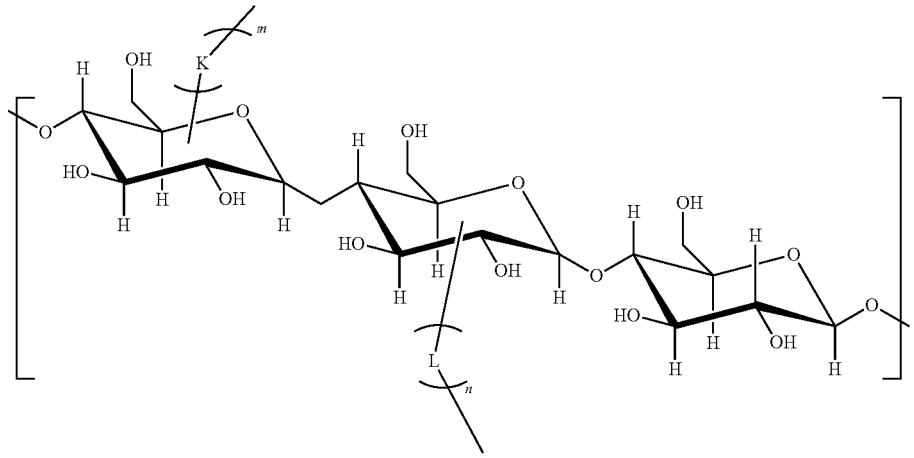

where m is the average number of repeat units of the first ethylenically unsaturated monomer $SM_1$, n is the average number of repeat units of the second ethylenically unsaturated monomer $SM_2$, different from $SM_1$, K is the moiety derived from the first ethylenically unsaturated synthetic monomer $SM_1$ and L is the moiety derived from the second ethylenically unsaturated synthetic monomer $SM_2$, It is important to note that the attachment point of the synthetic chain to the natural hydroxyl containing component may be at any carbon atom of the anhydroglucosee repeat unit. In addition, it is within the scope of this invention for one attachment point to be at a certain carbon (e.g., $C_2$) and the other attachment point be at a different carbon (e.g., $C_1$) of the same repeat unit. It is also possible for the attachment points to be on different repeat units of the same chain, such as shown in the above structure.

The resulting materials have the performance properties of synthetic polymers but are of lower cost and use readily available and environmentally friendly materials derived from renewable sources. These materials can be used in a variety of application areas, including, but not limited to, water treatment, detergent, oil field, dispersant and other aqueous treatment applications.

It has now been found that graft dendrite copolymers may be produced by polymerization, such as by metal ion catalyst redox initation, of two or more synthetic monomers when the two or more synthetic monomers are polymerized sequentially to the natural hydroxyl containing components. That is, a first synthetic monomer is polymerized in the presence of the natural hydroxyl containing component. Upon almost complete polymerization of the first monomer, the second monomer is added, along with additional initiator, and this second monomer is polymerized in the presence of the same natural hydroxyl containing component.

For purposes of this invention, almost complete polymerization is defined as greater than 90% of the first monomer is reacted and more preferably greater than 95% of the first monomer is reacted and most preferably greater than 99% of the first monomer is reacted before the second monomer is added. Accordingly, in an aspect, the resulting graft dendrite copolymer composition will contain a graft "dendrite" copolymer containing both synthetic monomers as synthetic chains covalently bonded to the natural hydroxyl containing component, with the proviso that each of these sequentially added monomers is attached to different locations of the natural hydroxyl containing component. One skilled in the art will also recognize that the graft dendrite copolymer composition may contain a certain amount of the unreacted natural hydroxyl containing component.

In an embodiment, if three different synthetic monomers, for example $SM_1$, $SM_2$, $SM_3$, are used then these three monomers can be added sequentially or alternatively two monomers can be added as a mixture and the third monomer can be added sequentially.

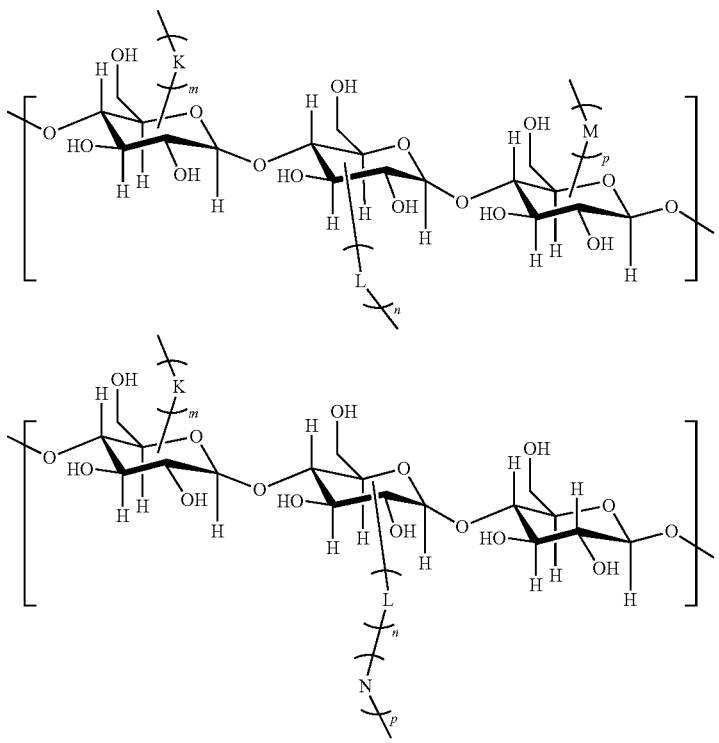

where m is the average number of repeat units of the first ethylenically unsaturated monomer $SM_1$, n is the average number of repeat units of the second ethylenically unsaturated monomer $SM_2$, p is the average number of repeat units of the second ethylenically unsaturated monomer $SM_3$, K is the moiety derived from the first ethylenically unsaturated synthetic monomer $SM_1$, L is the moiety derived from the second ethylenically unsaturated synthetic monomer $SM_2$ And M is the moiety derived from the second ethylenically unsaturated synthetic monomer $SM_3$.

In an embodiment of the invention, the graft dendrite copolymer composition may be an anionic graft dendrite copolymer or a non-anionic dendrite copolymer. In an embodiment, the non-anionic graft dendrite copolymer may be cationic, nonionic, amphoteric or zwitterionic or mixtures thereof.

In an embodiment, the ethylenically unsaturated monomers may be a combination of one or more types chosen from anionic, non-ionic or cationic monomers where each ethylenically unsaturated monomer is of the same type or a different type. For example, in an embodiment, $SM_1$ and $SM_2$ are both anionic and the graft dendrite copolymer is multi-anionic. In another embodiment, $SM_1$ and $SM_2$ are both cationic and the graft dendrite copolymer is multi-cationic. In yet another embodiment, $SM_1$ and $SM_2$ are both nonionic and the graft dendrite copolymer is multi-nonionic. In still another embodiment, where $SM_1$ and $SM_2$ are different types of monomers, $SM_1$ may be anionic and $SM_2$ may be nonionic or cationic, in which instances, the graft dendrite copolymer may be anionic or amphoteric, respectively. In still yet another embodiment, where $SM_1$ and $SM_2$ are different types of monomers, $SM_1$ may be cationic and $SM_2$ may be nonionic or anionic, in which instances, the graft dendrite copolymer may be cationic or amphoteric, respectively.

The term "graft dendrite copolymer", as defined herein, refers to a dendrite copolymer of two or more ethylenically unsaturated monomers located at different attachment points on the natural hydroxyl containing component as the backbone. For example, the monomers may be attached on different chains where each chain is attached to the natural hydroxyl containing component as the backbone. In an embodiment of the invention, the graft dendrite copolymer is believed to have the following structure:

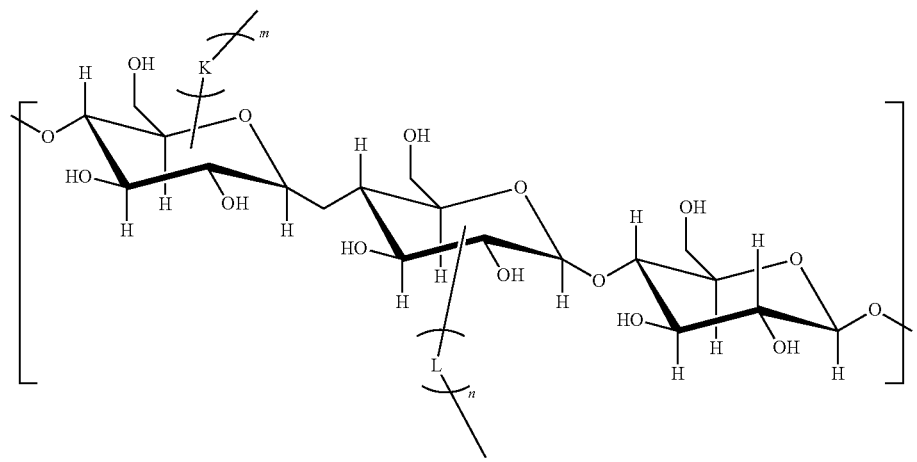

where m is the average number of repeat units of the first ethylenically unsaturated monomer $SM_1$, n is the average number of repeat units of the second ethylenically unsaturated monomer $SM_2$, K is the moiety derived from the first ethylenically unsaturated synthetic monomer $SM_1$ and L is the moiety derived from the second ethylenically unsaturated synthetic monomer $SM_2$.

In an embodiment, in addition to K and L, the graft dendrite copolymer may optionally contain moieties derived from other monomers, so long as K and L are different. In a further embodiment, the graft dendrite copolymer composition is preferably a homogeneous water soluble copolymer composition and not a dispersion or emulsion copolymer composition. Unlike homogeneous water soluble copolymer compositions, dispersion or emulsion copolymer compositions comprise suspended, or dispersed or emulsified polymer particles that are not water soluble. For purposes of the present application, water soluble is defined as having a solubility of greater than about 0.1 grams per 100 grams of water at 25° C. and preferably 1 gram per 100 grams of water at 25° C. and most preferably 10 grams per 100 grams of water at 25 C.

In an embodiment of the invention, the order of addition of the first and second synthetic monomers may be reversed. In an embodiment, the ethylenically unsaturated monomers may be a combination of one or more types chosen from anionic, non-ionic or cationic monomers where each ethylenically unsaturated monomer is of the same type or a different type.

In an embodiment of the invention, the initiator or initiator system used to produce the dendrite graft copolymers may be those traditionally used in grafting reactions. These are typically redox systems of a metal ion and hydrogen peroxide. These initiating systems will extract a proton from the natural hydroxyl containing component promoting the grafting reaction. In another aspect, the graft copolymers are made using free radical initiating systems such as ceric ammonium nitrate and Fe (II)/$H_2O_2$ (see, Würzburg, O. B., Modified Starches: Properties and Uses, *Grafted Starches*, Chpt. 10, pp. 149-72, CRC Press, Boca Raton (1986)).

Metal ion initiating systems, such as those containing Fe(II) salts or Ce(IV), may be used to create the graft dendrite copolymers. The graft dendrite copolymers may be produced by selectively generating initiation sites (e.g., free radicals) for the growth of monomer side chains from an existing polymer backbone, using conventional processes. (see e.g., CONCISE ENCYCLOPEDIA OF POLYMER SCIENCE AND ENGINEERING, J. I. Kroschwitz, ed., Wiley-Interscience, New York, p. 436 (1990)). In an embodiment, the metal ion containing systems are preferred to generate a free radical on the natural hydroxyl containing component. Accordingly, the graft dendrite copolymers are defined as a backbone of a natural hydroxyl containing component such as a polysaccharide with two or more side chains derived from synthetic monomers.

The mechanism for producing such "graft" dendrite copolymers is illustrated below.

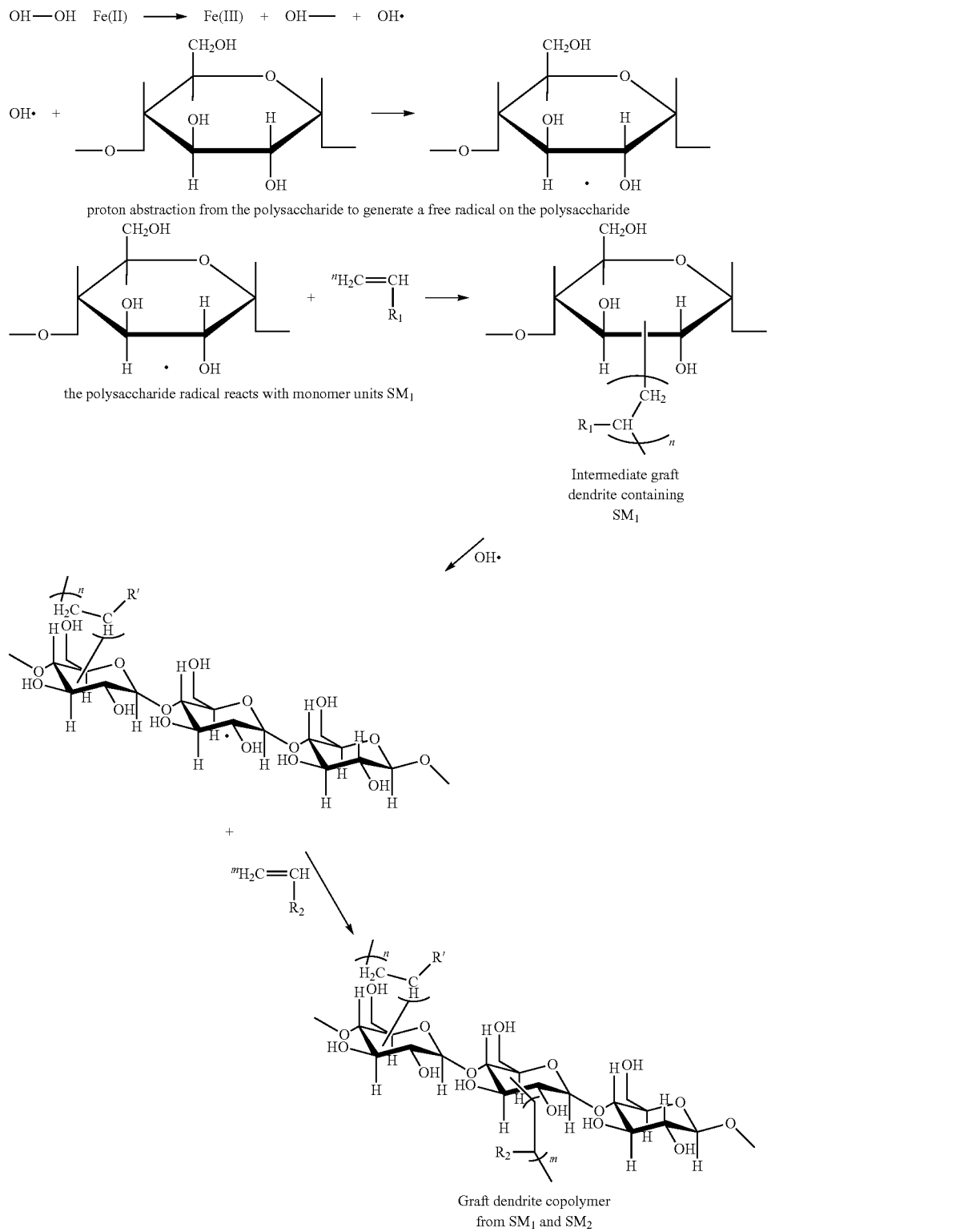

The term "natural hydroxyl containing component" as used herein, means any hydroxyl containing material obtained from a renewable source. In an embodiment of the invention, the natural hydroxyl containing components include, but are not limited, to small molecules such as glycerol, citric acid, lactic acid, tartaric acid, gluconic acid, ascorbic acid, glucoheptonic acid. The natural hydroxyl containing components may also include saccharides or derivatives thereof. Suitable saccharides include, for example, monosaccharides and disaccharides such as sugars for example glucose, fructose and maltose, as well as larger molecules such as oligosaccharides and polysaccharides (e.g., maltodextrins, corn syrups, and starches). Examples of these include sucrose, fructose, maltose, glucose and saccharose, as well as the reaction products of saccharides such as hydrogenation of starch hydrolysates such as mannitol, sorbitol maltitol and in particular hydrogenated corn syrups and maltodextrins and other reaction products such as polydextrose. The oligosaccharides, polysaccharides, hydrogenated corn syrups and maltodextrins and polydextroses are preferred. One skilled in the art will recognize that the oligosaccharides and polysaccharides can be produced by a variety of methods including acid or enzyme hydrolysis or combinations thereof.

In embodiments of the invention, polysaccharides useful in the present invention further include pyrodextrins. Pyrodextrins are made by heating acidified, commercially dry starch to a high temperature. Extensive degradation occurs initially due to the usual moisture present in starch. However, unlike the above reactions that are performed in aqueous solution, pyrodextrins are formed by heating powders. As moisture is driven off by the heating, hydrolysis stops and recombination of hydrolyzed starch fragments occur. This recombination reaction makes these materials distinct from maltodextrins, which are hydrolyzed starch fragments. The resulting pyrodextrin product also has much lower reducing sugar content, as well as color and a distinct odor.

Use of natural materials to produce a graft dendrite copolymer is attractive since it minimizes the use of monomers derived from petrochemical sources since these monomers are in short supply. For example, small molecule natural alcohols like glycerols are by-products of biodiesel production. Glycerol is also a by-product of oils and fats used in the manufacture of soaps and fatty acids. It can also be produced by fermentation of sugar. Citric acid is produced industrially by fermentation of crude sugar solutions. Lactic acid is produced commercially by fermentation of whey, cornstarch, potatoes, molasses, etc. Tartaric acid is one byproduct of the wine making process. In an embodiment of the invention, the small molecule natural alcohol is glycerol.

In an embodiment of the invention, the natural hydroxyl containing component is maltodextrin, pyrodextrin or a low molecular weight starch or oxidized starch. It has been found that the grafting reaction may not work well when the natural hydroxyl containing component is not soluble in the reaction system. For example, high molecular weight starches, such as those having molecular weights in the millions or those in granular form, are water dispersable and not water soluble. Accordingly, in embodiments of the invention, the average molecular weight of the natural hydroxyl containing component is preferably less than about 500,000 based on a starch standard. Starches having such exemplary molecular weights are water soluble. In another embodiment, the weight average molecular weight (Mw) of the natural hydroxyl containing component may be less than about 100,000. In yet another preferred embodiment, the weight average molecular weight of the natural hydroxyl containing component may be less than about 50,000. In yet another preferred embodiment, the weight average molecular weight of the natural hydroxyl containing component may be less than about 10,000. It has also been determined that for applications in which dispersancy and scale control is particularly desirable, a lower molecular weight, such as 10,000, of the natural hydroxyl containing component provides improved performance.

The molecular weight of the polysaccharide was determined by the procedure outlined below:
Eluent: 0.025 M $NaH_2PO_4$, 0.025 M $Na_2HPO_4$ and 0.01 M of Sodium Azide in HPLC grade water. This solution was filtered through a 0.2 μm filter.
Columns: 1×G6000PW×1 7.8 mm×30 cm, G4000PW×1 7.8×30 cm, G3000PW×1 7.8 mm×30 cm, Guard column is TSKgel Guard PW×1 6.0 mm×4 cm (all made by Tosoh Bioscience)
The column bank was controlled to 5° C. above ambient temperature. Usually 30° C.
Flow Rate: 1.0 ml/min
Detector: Refractive Index, Waters® Model 2414 Temperature controlled to 30° C.
Pump/Autosampler: Waters® e2695 Separation Module. Sample compartment temperature controlled to 25° C.
Primary Standards: HETA (Hydroxyethylstarch). Available from American Polymer Standards Corporation. (www.ampolymer.com)
5 standards. Prepare a 0.1% w/w in the mobile phase of each of the following:
1. Mw 9,600 Mn 5,400
2. Mw 25,900 Mn 10,600
3. Mw 51,100 Mn 34,300
4. Mw 114,300 Mn 58,000
5. Mw 226,800 Mn 95,900
Sample Preparation: The samples were prepared by dissolving the polymer in the mobile phase at a 0.1% concentration.
Injection Volume: 450 μl for the standard and sample.
The standards are injected and a first or second order calibration curve is built.
The curve with the best fit and within the range of the molecular weight of the unknown sample was then chosen.
Software: Empower® 2 by Waters Corporation
A calibration curve is first built with the samples of the standards. The molecular weight of the unknown sample is then determined by comparing its elution time with the elution time of the standards.

Polysaccharides useful in the present invention can also be derived from plant, animal and microbial sources. Examples of such polysaccharides include starch, cellulose, gums (e.g., gum arabic, guar and xanthan), alginates, pectin and gellan. Starches include those derived from maize and conventional hybrids of maize, such as waxy maize and high amylose (greater than 40% amylose) maize, as well as other starches such as potato, tapioca, wheat, rice, pea, sago, oat, barley, rye, and amaranth, including conventional hybrids or genetically engineered materials. Also included are hemicellulose or plant cell wall polysaccharides such as d-xylans. Examples of plant cell wall polysaccharides include arabino-xylans such as corn fiber gum, a component of corn fiber.

When the polysaccharide is a gum, applicable bases that can be used herein include polygalactomannans (heteropolysaccharides composed principally of long chains of β-d-mannopyranosyl units to which single unit side chains of α-d-galactopyranosyl units are joined). Also included are degraded gum products resulting from the hydrolytic action of acid, heat, shear and/or enzyme; oxidized gums; and derivatized gums. Suitable gum bases include guar, locust bean, tara and fenugreek gums.

Other suitable polysaccharide bases useful in the present invention include, for example, pullulan, chitin, chitosan, gum arabic, agar, algin, carrageenan, xanthan, gellan, welan, rhamsan, curdlan scleroglucan, tamarind gum, and hemicelluloses such as arabinogalactans and corn fiber gum and their derivatives.

When the polysaccharide is cellulose, applicable bases useful herein include cellulose and cellulose derivatives such as water soluble cellulose ethers (e.g., carboxymethylcellulose and alkyl and hydroxyalkylcelluloses such as methylcellulose, hydroxypropyl methylcellulose, hydroxyethyl cellulose, hydroxyethyl methylcellulose, hydroxybutyl methylcellulose, and ethyl hydroxyethyl cellulose).

Suitable polysaccharides should preferably be water soluble during the reaction. This implies that the polysaccharides either have a molecular weight low enough to be water soluble or can be hydrolyzed in situ during the reaction to become water soluble. For example, non-degraded starches are not water soluble. However, degraded starches are water soluble and are preferred. Furthermore, water solubility may be achieved by chemical modification for example cellulose to carboxymethyl cellulose.

In an embodiment of the invention, degraded polysaccharides according to the present invention can have a number average molecular weight of about 100,000 or lower. In an embodiment, the number average molecular weight (Mn) of the sulfonated graft copolymer is about 25,000 or less. In another aspect, the degraded polysaccharides have a number average molecular weight of about 10,000 or less.

In an embodiment of the invention, the natural hydroxyl containing component is a polysaccharide comprising maltodextrin. Maltodextrins are polymers having d-glucose units linked primarily by α-1,4 bonds and a dextrose equivalent ('DE') of about 20 or less. Dextrose equivalent is a measure of the extent of starch hydrolysis. It is determined by measuring the amount of reducing sugars in a sample relative to dextrose (glucose). The DE of dextrose is 100, representing 100% hydrolysis. The DE value gives the extent of hydrolysis (e.g., 10 DE is more hydrolyzed than 5 DE maltodextrin). Maltodextrins are available as a white powder or concentrated solution and are prepared by the partial hydrolysis of starch with acid and/or enzymes.

Polysaccharides useful in the present invention can further include corn syrups. Corn syrups are defined as degraded starch products having a DE of 27 to 95. Examples of specialty corn syrups include high fructose corn syrup and high maltose corn syrup. Monosaccharides and oligosaccharides such as galactose, mannose, sucrose, maltose, fructose, ribose, trehalose, lactose, etc., can be used.

In an embodiment of the invention, the polysaccharide has a DE of about 65 or less, 45 or less, 20 or less, in another embodiment a DE of about 15 or less and in still another embodiment a DE of about 5 or less and a DE about 1.

As noted above, the natural hydroxyl containing components also may include cellulose and its derivatives, but they may also include inulin and its derivatives, such as carboxymethyl inulin. The cellulosic derivatives include plant heteropolysaccharides commonly known as hemicelluloses which are by products of the paper and pulp industry. Hemicelluloses include xylans, glucuronoxylans, arabinoxylans, arabinogalactans glucomannans, and xyloglucans. Xylans are the most common heteropolysaccharide and are preferred. Furthermore, these natural hydroxyl containing components also include lignin and its derivatives, such as lignosulfonates In an embodiment of the invention, cellulosic derivatives such as heteropolysaccharides such as xylans and lignin and its derivatives may be present in an amount of from about 0.1% to about 98% by weight, based on the total amount of the graft copolymer. In an embodiment of this invention the natural hydroxyl containing components may be maltodextrins, pyrodextrins and chemically modified versions of maltodextrins and pyrodextrins. In another embodiment, the natural hydroxyl containing component may be cellulose or inulin or chemically modified cellulose such as carboxymethyl cellulose, hydroxy ethyl cellulose, hydroxyl propyl cellulose, and ethyl/methyl derivatives of these celluloses or inulin or carboxy methyl inulin or a heteropolysaccharide such as xylan or a lignin derivative, such as lignosulfonate. In the case of cellulose or chemically modified celluloses, they are depolymerized to low molecular weights before being used to synthesize the graft dendrite copolymer compositions of this invention.

The natural hydroxyl containing components can be used as obtained from their natural source or they can be chemically modified. Chemical modification includes hydrolysis by the action of acids, enzymes, oxidizers or heat, esterification or etherification. The modified natural hydroxyl containing components, after undergoing chemical modification may be cationic, anionic, non-ionic or amphoteric or hydrophobically modified. Such chemical modifications and the like pertaining to the natural hydroxyl containing components are detailed in US Patent application publication number US 2007-0021577 A1, which is incorporated by reference in its entirety herein. Accordingly, the natural hydroxyl containing components suitable for use in the present invention include oxidatively, hydrolytically or enzymatically degraded monosaccharides, oligosaccharides and polysaccharides, as well as chemically modified monosaccharides, oligosaccharides and polysaccharides. Chemically modified derivatives include carboxylates, sulfonates, phosphates, phosphonates, aldehydes, silanes, alkyl glycosides, alkyl-hydroxyalkyls, carboxy-alkyl ethers and other derivatives. The polysaccharide can be chemically modified before, during or after the polymerization reaction.

In an embodiment of the invention, polysaccharides can be modified or derivatized by etherification (e.g., via treatment with propylene oxide, ethylene oxide, 2,3-epoxypropyl trimethyl ammonium chloride), esterification (e.g., via reaction with acetic anhydride, octenyl succinic anhydride ('OSA')), acid hydrolysis, dextrinization, oxidation or enzyme treatment (e.g., starch modified with α-amylase, β-amylase, pullanase, isoamylase or glucoamylase), or various combinations of these treatments. These treatments can be performed before or after the polymerization process.

The polysaccharides can be modified with cationic, anionic, amphoteric, zwitterionic, hydrophobic and nonionic groups, as well as combinations of such groups. Modification of the starch can be carried out by well known chemical reactions with reagents containing groups such as amino, imino, ammonium, sulfonium or phosphonium groups as disclosed, for example, in Modified Starches: Properties and Uses, (1986). Such derivatives include those containing nitrogen containing groups comprising primary, secondary, tertiary and quaternary amines, as well as sulfonium and phosphonium groups attached through either ether or ester linkages.

Virtually any ethylenically unsaturated or polymerizable monomer can be used to produce the graft dendrite copolymers of the present invention. Monomers which promote water solubility or water dispersabilty of the final product are preferred. Furthermore, there is essentially no limit on the number of monomers that can be used.

In an embodiment of the invention, the ethylenically unsaturated monomer is anionic. Accordingly, the graft dendrite copolymer comprises a synthetic polymer produced from at least one anionic ethylenically unsaturated monomer grafted to a natural hydroxyl containing component.

As used herein, the term "anionic ethylenically unsaturated monomer" means an ethylenically unsaturated monomer which is capable of introducing a negative charge to the graft dendrite copolymer. These anionic ethylenically unsaturated monomers can include, but are not limited to, acrylic acid, methacrylic acid, ethacrylic acid, α-chloro-acrylic acid, α-cyano acrylic acid, β-methyl-acrylic acid (crotonic acid), α-phenyl acrylic acid, β-acryloxy propionic acid, sorbic acid, α-chloro sorbic acid, angelic acid, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, 2-acrylamido-2-methyl propane sulfonic acid and its sodium salt (AMPS), vinyl sulfonic acid, sodium methallyl sulfonate, sulfonated styrene, (meth)allyloxybenzene sulfonic acid, vinyl phosphonic acid, sodium 1-allyloxy 2 hydroxy propyl sulfonate and maleic acid and their salts. Moieties such as maleic anhydride or acrylamide that can be derivatized (hydrolyzed) to moieties with a negative charge are also suitable. Combinations of anionic ethylenically unsaturated monomers can also be used. In an embodiment of the invention, the anionic ethylenically unsaturated monomer may be acrylic acid, maleic acid, methacrylic acid, itaconic acid, 2-acrylamido-2-methyl propane sulfonic acid and their salts or mixtures of the above-described monomers. In an embodiment of the invention, the first synthetic monomer $SM_1$ is acrylic acid, itaconic acid, maleic acid, methacrylic acid or its salts or combinations thereof and the second synthetic monomer, $SM_2$, is 2-acrylamido-2-methyl propane sulfonic acid or its salts.

Suitable synthetic monomers for use in the present invention may also optionally include hydrophobic monomers. These hydrophobic monomers may be used in amounts such that the resulting dendrite copolymer composition is still water soluble. These hydrophobic monomers include saturated or unsaturated alkyl, hydroxyalkyl, alkylalkoxy groups, arylalkoxy, alkarylalkoxy, aryl and aryl-alkyl groups, siloxane etc. Examples of hydrophobic monomers include styrene, α-methyl styrene, methyl methacrylate, methyl acrylate, 2-ethylhexyl acrylate, octyl acrylate, lauryl acrylate, stearyl acrylate, behenyl acrylate, 2-ethylhexyl methacrylate, octyl methacrylate, lauryl methacrylate, stearyl methacrylate, behenyl methacrylate, 2-ethylhexyl acrylamide, octyl acrylamide, lauryl acrylamide, stearyl acrylamide, behenyl acrylamide, propyl acrylate, butyl acrylate, pentyl acrylate, hexyl acrylate, 1-vinyl naphthalene, 2-vinyl naphthalene, 3-methyl styrene, 4-propyl styrene, t-butyl styrene, 4-cyclohexyl styrene, 4-dodecyl styrene, 2-ethyl-4-benzyl styrene, and 4-(phenyl butyl) styrene. The hydrophobic monomers include those containing silane groups such as vinyl trimethoxy silane, vinyl triethoxy silane, vinyl triisopropoxy silane, vinyl triacetoxy silane, vinyl tris (2 ethoxymethoxy) silane, vinyl methyl dimethoxy silane, gamma methacryloxypropyltrimethoxy silane and others. One skilled in the art will recognize that these silane monomers can be hydrolyzed to silanol groups which are useful in this invention.

In another aspect, the present invention relates to graft dendrite copolymer that contain at least one non-anionic ethylenically unsaturated monomer. As used herein, non-anionic ethylenically unsaturated monomers include those that are not anionic. That is, these non-anionic ethylenically unsaturated monomers may include, but are not limited to, cationic ethylenically unsaturated monomers, nonionic ethylenically unsaturated monomers, amphoteric ethylenically unsaturated monomers and zwitterionic enthylenically unsaturated monomers and mixtures thereof. A non-anionic graft dendrite copolymer, as used herein, comprises a synthetic polymer produced from at least one cationic ethylenically unsaturated monomer or at least one nonionic ethylenically unsaturated monomer grafted on to a natural hydroxyl containing component.

As used herein, the term "cationic ethylenically unsaturated monomer" means an ethylenically unsaturated monomer which is capable of introducing a positive charge to the non-anionic graft copolymer composition. Examples of cationic monomers include, but are not limited to, acrylamidopropyltrimethyl ammonium chloride (APTAC), methacrylamidopropyltrimethyl ammonium chloride (MAPTAC), diallyldimethyl ammonium chloride (DADMAC), acryloyloxyethyl trimethyl ammonium chloride (AETAC), methacryloyloxyethyl trimethyl ammonium chloride. In an embodiment of the present invention, the cationic ethylenically unsaturated monomer has at least one amine functionality. Cationic derivatives of these non-anionic graft dendrite copolymers may be formed by forming amine salts of all or a portion of the amine functionality, by quaternizing all or a portion of the amine functionality to form quaternary ammonium salts, or by oxidizing all or a portion of the amine functionality to form N-oxide groups.

As used herein, the term "amine salt" means the nitrogen atom of the amine functionality is covalently bonded to from one to three organic groups and is associated with an anion.

As used herein, the term "quaternary ammonium salt" means that a nitrogen atom of the amine functionality is covalently bonded to four organic groups and is associated with an anion. These cationic derivatives can be synthesized by functionalizing the monomer before polymerization or by functionalizing the polymer after polymerization. These cationic ethylenically unsaturated monomers include, but are not limited to, N,N dialkylaminoalkyl(meth)acrylate, N,N dialkylaminoalkylacrylate, N-alkylaminoalkyl(meth)acrylate, N,N dialkylaminoalkylacrylamide N,N dialkylaminoalkyl(meth)acrylamide and N-alkylaminoalkyl(meth)acrylamide, where the alkyl groups are independently $C_{1-18}$ cyclic compounds such as 1-vinyl imidazole and the like. Aromatic amine containing monomers, such as vinyl pyridine may also be used. Furthermore, monomers such as vinyl formamide, vinyl acetamide and the like which generate amine moieties on hydrolysis may also be used. Preferably the cationic ethylenically unsaturated monomer is N,N-dimethylaminoethyl methacrylate, tert-butylaminoethylmethacrylate and N,N-dimethylaminopropyl methacrylamide. In an embodiment of the invention, the amine monomer is chosen from N,N-dimethylaminoethyl methacrylate, N,N-dimethylaminopropyl methacrylamide, and N,N-diethylaminoethyl methacrylate. In an embodiment, the vinyl pyridine and other amine monomers can be oxidized or quaternized.

Cationic ethylenically unsaturated monomers that may be used are the quaternized derivatives of the above monomers as well as diallyldimethylammonium chloride also known as dimethyldiallylammonium chloride, (meth)acrylamidopropyl trimethylammonium chloride, 2-(meth)acryloyloxy ethyl trimethyl ammonium chloride, 2-(meth)acryloyloxy ethyl trimethyl ammonium methyl sulfate, 2-(meth)acryloyloxyethyltrimethyl ammonium chloride, N,N-Dimethylaminoethyl (meth)acrylate methyl chloride quaternary, methacryloyloxy ethyl betaine as well as other betaines and sulfobetaines, 2-(meth)acryloyloxy ethyl dimethyl ammonium hydrochloride, 3-(meth)acryloyloxy ethyl dimethyl ammonium hydroacetate, 2-(meth)acryloyloxy ethyl dimethyl cetyl ammonium chloride, 2-(meth)acryloyloxy ethyl diphenyl ammonium chloride and others. In an embodiment, cationic ethylenically unsaturated monomers suitable for use in the present invention are the quaternized derivatives of N,N dialkylaminoalkyl(meth)acrylate, N,N dialkylamino alkylacrylate, N,N dialkylaminoalkylacrylamide and N,N dialkylaminoalkyl(meth)acrylamide, One skilled in the art will recognize that these can be quaternized with methyl chloride (as mentioned above), but they may also be quaternized with dimethylsulfate, diethyl sulfate, ethyl chloride and benzyl chloride and other quaternizing agents.

In an embodiment of the invention, when at least one of the ethylenically unsaturated monomers is cationic, the dendrite copolymer composition is substantially free of acrylamide or methacrylamide. Substantially free means that the dendrite copolymer composition contains less than about 1% of these monomers, preferably less than about 0.1% of these monomers and most preferably less than about 0.001% of these monomers. While in this embodiment, the dendrite copolymer composition is substantially free of acrylamide or methacrylamide, the dendrite copolymer composition may contain derivatives of acrylamide or methacrylamide such as N,N dimethylacrylamide and other derivatives mentioned in this application.

In another embodiment of the invention, when at least one of the ethylenically unsaturated monomers is cationic, the copolymer composition comprises about 20 weight percent or greater of the cationic ethylenically unsaturated monomer based on the weight of the dendrite copolymer composition. In a further embodiment, the copolymer composition comprises about 25 weight percent or greater of the cationic ethylenically unsaturated monomer, and in yet another embodiment, the copolymer composition comprises about 30 weight percent or greater of the cationic ethylenically unsaturated monomer, In still yet another embodiment, when at least one of the ethylenically unsaturated monomers is cationic, the copolymer composition is substantially free of a crosslinking agent. Substantially free means that the dendrite copolymer composition contains less than about 1% of a crosslinking agent, preferably less than about 0.1% of a crosslinking agent and most preferably less than about 0.001% of a crosslinking agent.

As used herein, the term "nonionic ethylenically unsaturated monomer" means an ethylenically unsaturated monomer which does not introduce a charge in to the non-anionic graft copolymer composition. These nonionic ethylenically unsaturated monomers include, but are not limited to, $C_1$-$C_6$ alkyl esters of (meth)acrylic acid and the alkali or alkaline earth metal or ammonium salts thereof, acrylamide and the $C_1$-$C_6$ alkyl-substituted acrylamides, the N-alkyl-substituted acrylamides and the N-alkanol-substituted acrylamides, hydroxyl alkyl acrylates and acrylamides. Also suitable are the $C_1$-$C_6$ alkyl esters and $C_1$-$C_6$ alkyl half-esters of unsaturated vinylic acids, such as maleic acid and itaconic acid, and $C_1$-$C_6$ alkyl esters of saturated aliphatic monocarboxylic acids, such as acetic acid, propionic acid and valeric acid. In embodiment, the nonionic ethylenically unsaturated monomer is chosen from acrylamide, methacrylamide, N alkyl(meth)acrylamide, N,N dialkyl(meth)acrylamide such as N,N dimethylacrylamide, hydroxyalkyl(meth)acrylates, alkyl(meth)acrylates such as methylacrylate and methylmethacrylate, vinyl acetate, vinyl morpholine, vinyl pyrrolidone, vinyl caprolactum, ethoxylated alkyl, alkaryl or aryl monomers such as methoxypolyethylene glycol (meth)acrylate, allyl glycidyl ether, allyl alcohol, glycerol (meth)acrylate, monomers containing silane, silanol and siloxane functionalities and others. The nonionic ethylenically unsaturated monomer is preferably water soluble. In a further embodiment, the nonionic ethylenically unsaturated monomer is chosen from acrylamide, methacrylamide, N methyl(meth)acrylamide, N,N dimethyl(meth)acrylamide, methyl methacrylate, methyl acrylate, hydroxyethyl (meth)acrylate and hydroxypropyl (meth)acrylate, N,N dimethylacrylamide, N,N diethylacrylamide, N-isopropylacrylamide and acryloyl morpholin vinyl pyrrolidone and vinyl caprolactum.

In an embodiment of the invention, the first synthetic monomer, $SM_1$, is anionic and is acrylic acid, itaconic acid, maleic acid, methacrylic acid, 2-acrylamido-2-methyl propane sulfonic acid or its salts and the second monomer, $SM_2$, is cationic and is methacrylamidopropyltrimethyl ammonium chloride (MAPTAC), diallyldimethyl ammonium chloride (DADMAC), acryloyloxyethyl trimethyl ammonium chloride (AETAC), methacryloyloxyethyl trimethyl ammonium chloride or combinations thereof.

In another aspect, the invention relates to a process to produce the graft dendrite copolymer. The process comprises polymerizing at least one first ethylenically unsaturated monomer in the presence of a natural hydroxyl containing component until the reaction is substantially complete, for example when less than about 10%, or less than about 1%, of the at least one first monomer is left unreacted and then polymerizing at least one second ethylenically unsaturated monomer in the presence of the reaction product of the first monomer and the natural hydroxyl containing component. In another aspect, the invention is directed to the product produced by the aforementioned process.

In an embodiment of the invention, the graft dendrite copolymer may contain about 1 to about 99.5 weight percent of the natural hydroxyl containing component based on the weight of the graft dendrite copolymer. In another embodiment, the dendrite graft copolymer may contain at least about 10 weight percent, preferably at least about 50 weight percent and most preferably at least about 75 weight percent of the natural hydroxyl containing component based on the weight of the graft dendrite copolymer In another embodiment, the dendrite graft copolymer may contain at most about 99.5 weight percent, preferably at most about 95 weight percent and most preferably at most about 90 weight percent of the natural hydroxyl containing component based on the weight of the graft dendrite copolymer composition.

In embodiments of the invention, the graft dendrite copolymer can be used as a constituent of a composition for a number of different applications including, but not limited to, cleaning, laundry, automatic dish washing (ADW), superabsorbent, fiberglass binder, rheology modifier, oil field, water treatment, dispersant, cementing and concrete compositions. For cleaning applications, the compositions may include, but are not limited to, detergent, fabric cleaner, automatic dishwashing detergent, rinse aids, glass cleaner, fabric care formulation, fabric softener, flocculants, coagulants, emulsion breakers, alkaline and acidic hard surface cleaners, laundry detergents and others. The compositions can also be used to clean surfaces in industrial and institutional cleaning applications. In an exemplary embodiment for automatic dishwashing detergent formulations, such formulations include phosphate, low phosphate and "zero" phosphate built formulations, in which the detergent is substantially free of phosphates. As used herein, low phosphate means less than 1500 ppm phosphate in the wash, in another embodiment less than about 1000 ppm phosphate in the wash, and in still another embodiment less that 500 ppm phosphate in the wash.

The graft dendrite copolymers can also be used as scale control agents in cleaning, laundry, ADW, oil field, water treatment, and in any other aqueous system where scale buildup is an issue. The scales controlled include, but are not limited to, carbonate, sulfate, phosphate or silicate based scales such as calcium sulfate, barium sulfate, calcium ortho and polyphosphate, tripolyphosphate, magnesium carbonate, magnesium silicate and others.

In further embodiments, the graft dendrite copolymers can also be used as dispersants in cleaning, oil field and water treatment applications, paint and coatings, paper coatings and other applications. These graft dendrite copolymers can be used to disperse particulates including, but not limited to, minerals, clays, salts, metallic ores, metallic oxides, dirt, soils, talc, pigments, titanium dioxide, mica, silica, silicates, carbon black, iron oxide, kaolin clay, calcium carbonate, synthetic calcium carbonates, precipitated calcium carbonate, ground calcium carbonate, precipitated silica, kaolin clay or combinations thereof.

Suitable adjunct ingredients for use in the present invention include, but are not limited to, water, surfactants, builders, phosphates, sodium carbonate, citrates, enzymes, buffers, perfumes, anti-foam agents, ion exchangers, alkalis, antiredeposition materials, optical brighteners, fragrances, dyes, fillers, chelating agents, fabric whiteners, brighteners, sudsing control agents, solvents, hydrotropes, bleaching agents, bleach precursors, buffering agents, soil removal agents, soil release agents, fabric softening agent, opacifiers, water treatment chemicals, corrosion inhibitors, orthophosphates, zinc compounds, tolyltriazole, minerals, clays, salts, metallic ores, metallic oxides, talc, pigments, titanium dioxide, mica, silica, silicates, carbon black, iron oxide, kaolin clay, modified kaolin clays, calcium carbonate, synthetic calcium carbonates, fiberglass, cement and aluminum oxide. The surfactants can be anionic, non-ionic, such as low foaming non-ionic surfactants, cationic or zwitterionic. In an embodiment of the invention, the chelants may be glutamic acid N,N-diacetic acid (GLDA) and methylglycine N,N-diacetic acid (MGDA) and the like.

Some other oil field uses for the graft dendrite copolymers of this invention include additives in cementing, drilling muds, dispersancy and spacer fluid applications. Often, the water encountered in oil field applications is sea water or brines from the formation. The water encountered in the oilfield can be very brackish. Hence, the polymers may also desirably be soluble in many brines and brackish waters. These brines may be sea water which contains about 3.5 percent NaCl by weight or more severe brines that contain, for example, up to 3.5% KCl, up to 25% NaCl and up to 20% $CaCl_2$. Therefore, the polymers should be soluble in these systems for them to be effective as, for example, scale inhibitors. It has further been found that the higher the solubility of the graft dendrite copolymers in the brine, the higher the compatibility. The composition of synthetic seawater, moderate and severe calcium brines which are typical brines encountered in the oilfield is listed in Table 1 below.

the carrier fluid is water or brines or methanol. Methanol is often used to prevent the formation of methane hydrate (also known as methane clathrate or methane ice) structures downhole. In another embodiment of this invention, the graft dendrite copolymers may be soluble in methanol. Thus, the scale inhibiting polymers can be introduced in to the well bore in the methanol line. This is particularly advantageous since there is fixed number of lines that run in to the wellbore and this combination eliminates the need for another line.

In an embodiment of the invention the graft dendrite copolymers can be uniformly mixed or blended with builders or chelating agents and then processed into powders or granules. For example, compositions including the graft dendrite copolymers of the present invention may include alkali metal or alkali-metal earth carbonates, citrates or silicates as exemplary builders suitable for use in detergent formulations. The term alkali metals are defined as the Group IA elements, such as lithium, sodium and potassium, whereas the alkali-metal earth metals are the Group IIA elements which include beryllium, magnesium and calcium.

Powders as used herein are defined as having an average particle size of less than about 300 microns, whereas granules are particles of an average size of greater than about 300 microns. By uniformly mixing or blending the graft dendrite copolymer with the builder or chelating agent, the particles or granules provide less hygroscopic properties and afford easier handling and free flowing powders. Free flowing as used in this application are powders or granules that do not clump or fuse together. In an embodiment of this invention, the graft polymer is an anionic graft copolymer. In another embodiment of this invention, the builders or chelating agents that can be blended with the graft dendrite copolymer are sodium or potassium carbonate, sodium or potassium silicate sodium or potassium citrate or glutamic acid N,N-diacetic acid (GLDA) or and methylglycine N,N-diacetic acid (MGDA).

In exemplary embodiments, the graft dendrite copolymers can also be used in fabric softener compositions as well as fabric care compositions. Suitable fabric softener formulations contain fabric softener actives, water, surfactants, electrolyte, phase stabilizing polymers, perfume, nonionic surfactant, non-aqueous solvent, silicones, fatty acid, dye, preservatives, optical brighteners, antifoam agents, and mixtures thereof. These fabric softener actives include, but are not limited, to diester quaternary ammonium compounds such as

TABLE 1

Typical brines encountered in the oilfield.
Brine preparation

| | grams per liter | | | ppm | | |
|---|---|---|---|---|---|---|
| Brine number and description | NaCl | $CaCl_2 \cdot 2H_2O$ | $MgCl_2 \cdot 6H_2O$ | Na | Ca | Mg |
| 1  synthetic seawater | 24.074 | 1.61 | 11.436 | 9471 | 439 | 1368 |
| 2  moderate calcium brine | 63.53 | 9.19 | | 24992 | 2506 | 0 |
| 3  severe calcium brine | 127.05 | 91.875 | | 49981 | 25053 | 0 |

As described in Table 1, sea water contains around 35 grams per liter of a mixture of salts. The moderate and severe calcium brines contain around 70 and 200 grams per liter of a mixture of salts respectively.

In oil field applications, the scale inhibitor may be injected or squeezed or may be added topside to the produced water. Accordingly, embodiments of the invention also include mixtures of the graft dendrite copolymer and a carrier fluid. The carrier fluid may be water, glycol, alcohol or oil. Preferably, ditallowoyloxyethyl dimethyl ammonium chloride, dihydrogenated-tallowoyloxyethyl dimethyl ammonium chloride, dicanola-oyloxyethyl dimethyl ammonium chloride, ditallow dimethyl ammonium chloride, triethanolamine ester quats such as di-(hydrogenated tallowoyloxyethyl)-N,N-methylhydroxyethylammonium methylsulfate and di-(oleoyloxyethyl)-N, N-methylhydroxyethylammonium methylsulfate as well as others such as tritallow methyl ammonium chloride, methyl bis(tallow amidoethyl)-2-hydroxyethyl ammonium methyl sulfate, methyl bis(hydrogenated tallow amidoethyl)-2-hydroxyethyl ammonium methyl sulfate, methyl bis(oleyl amidoethyl)-2-hydroxyethyl ammonium methyl sulfate, ditallowoyloxyethyl dimethyl ammonium methyl sulfate, dihydrogenated-tallowoyloxyethyl dimethyl ammonium chloride, dicanola-oyloxyethyl dimethyl ammonium chloride, N-tallowoyloxyethyl-N-tallowoylaminopropyl methyl amine, 1,2-bis(hardened tallowoyloxy)-3-trimethylammonium propane chloride, dihardened tallow dimethyl ammonium chloride and mixtures thereof.

The preferred actives are diester quaternary ammonium (DEQA) compounds which are typically made by reacting alkanolamines such as MDEA (methyldiethanolamine) and TEA (triethanolamine) with fatty acids. Some materials that typically result from such reactions include N,N-di(acyl-oxyethyl)-N,N-dimethylammonium chloride or N,N-di(acyloxyethyl)-N,N-methylhydroxyethylammonium methylsulfate wherein the acyl group is derived from animal fats, unsaturated, and polyunsaturated, fatty acids, e.g., oleic acid, and/or partially hydrogenated fatty acids, derived from vegetable oils and/or partially hydrogenated vegetable oils, such as, canola oil, safflower oil, peanut oil, sunflower oil, corn oil, soybean oil, tall oil, rice bran oil, and the like. Those skilled in the art will recognize that active softener materials made from such process can comprise a combination of mono-, di-, and tri-esters depending on the process and the starting materials.

As used herein, the term "fabric care formulations" include, but are not limited to, formulations used to treat fabric to improve fabric softness, shape retention, fabric elasticity, fabric tensile strength, fabric tear strength, fabric lubrication, fabric relaxation, durable press, wrinkle resistance, wrinkle reduction, ease of ironing, abrasion resistance, fabric smoothing, anti-felting, anti-pilling, crispness, appearance enhancement, appearance rejuvenation, color protection, color rejuvenation, anti-shrinkage, static reduction, water absorbency or repellency, stain repellency, refreshing, antimicrobial, odor resistance, and mixtures thereof. In addition to the non-anionic graft copolymers, the fabric care formulations may contain ingredients such as cationic surfactants, amphoteric surfactants, fabric softener actives, sucrose esters, softening agents, other fabric care agents, dispersing media, such as water, alcohols, diols; emulsifiers, perfumes, wetting agents, viscosity modifiers, pH buffers, antibacterial agents, antioxidants, radical scavengers, chelants, antifoaming agents, and mixtures thereof.

In further embodiments of the invention, the graft dendrite copolymers can be used as flocculants and coagulants for sludge dewatering and water clarification in waste water treatment applications. Further, domestic and industrial sewage contains suspended matter which must be removed. The suspended particles are predominantly stabilized due to their net negative surface charge. The graft dendrite copolymers disrupt this negative charge and enable removal of the suspended solids from the water. In still further embodiments, the graft dendrite copolymers function as emulsion breakers for oil in water emulsions. These are useful in waste water treatment applications to comply with the limitations of fats oil and greases in the discharge water. In addition, the graft dendrite copolymers function as reverse emulsion breakers in the oil field. In this application, small amounts of oil droplets are removed from the water continuous phase before the water can be safely returned to the environment. Additionally, graft dendrite copolymers of the invention can be utilized in applications requiring film forming characteristics, such as in personal care and/or cosmetic applications.

The graft dendrite copolymers can be used in cosmetic and personal care compositions. Cosmetic and personal care compositions include, for example, skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with AHA and BHA and hair fixatives such as sprays, gels, mousses, pomades, and waxes, including low VOC hair fixatives and sunscreens. These cosmetic and personal care compositions may be in any form, including without limitation, emulsions, gels, liquids, sprays, solids, mousses, powders, wipes, or sticks.

The cosmetic and personal care compositions contain suitable "cosmetic and personal care actives". Suitable cosmetic and personal care active agents include, for example, sunscreen agents or actives, aesthetic enhancers, conditioning agents, anti-acne agents, antimicrobial agents, anti-inflammatory agents, analgesics, anti-erythemal agents, antipruritic agents, antiedemal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self tanning agents, coenzyme Q10, niacinimide, capcasin, caffeine, and any combination of any of the foregoing.

Suitable sunscreen agents or actives useful in the present invention include any particulate sunscreen active that absorbs, scatters, or blocks ultraviolet (UV) radiation, such as UV-A and UV-B. Non-limiting examples of suitable particulate sunscreen agents include clays, agars, guars, nanoparticles, native and modified starches, modified cellulosics, zinc oxide, and titanium dioxide and any combination of the foregoing. Modified starches include, for example, DRY-FLO®PC lubricant (aluminum starch octenylsuccinate), DRY-FLO® AF lubricant (corn starch modified), DRY-FLO® ELITE LL lubricant (aluminum starch octenylsuccinate (and) lauryl lysine), DRY-FLO® ELITE BN lubricant (aluminum starch octenylsuccinate (and) boron nitride), all commercially available from National Starch and Chemical Company.

The sunscreen agents may include those that form a physical and/or chemical barrier between the UV radiation and the surface to which they are applied. Non-limiting examples of suitable sunscreen agents include ethylhexyl methoxycinnamate (octinoxate), ethylhexyl salicylate (octisalate), butylmethoxydibenzoylmethane, methoxydibenzoylmethane, avobenzone, benzophenone-3 (oxybenzone), octocrylene, aminobenzoic acid, cinoxate, dioxybenzone, homosalate, methyl anthranilate, octocrylene, octisalate, oxybenzone, padimate O, phenylbenzimidazole sulfonic acid, sulisobenzone, trolamine salicylate and any combination of any of the foregoing The cosmetic and personal care compositions can optionally include one or more aesthetic enhancers (i.e., a material that imparts desirable tactile, visual, taste and/or olfactory properties to the surface to which the composition is applied) and can be either hydrophilic or hydrophobic. Non-limiting examples of commercial aesthetic enhancers together with their NCI names that are optionally suitable for use in the present invention include PURITY®21C starch (zea maize (corn) starch) and TAPIOCA PURE (tapioca starch), as well as combinations thereof, that are available from the National Starch and Chemical Company.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cetrimonium chloride; diphenyl dimethicone; propylene glycol; glycerin; hydroxyalkyl urea; tocopherol; quaternary amines; and any combination thereof.

The cosmetic and personal care compositions can optionally include one or more adjuvants, such as pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

The cosmetic and personal care compositions may also contain preservatives. Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylchloroisothiazolinone, methylisothiazolinone, and any combination thereof. In an embodiment of the invention, the cosmetic and personal care composition generally contains from about 0.001% to about 20% by weight of preservatives, based on 100% weight of total composition. In another embodiment, the composition contains from about 0.1% to about 10% by weight of preservatives, based on 100% weight of total composition.

The cosmetic and personal care compositions may optionally contain thickeners or gelling agents. Examples of such gelling agents include, but are not limited to, synthetic polymers such as the acrylic-based Carbopol® series of thickeners available from B. F. Goodrich, Cleveland, Ohio and associative thickeners such as Aculyn™, available from Rohm & Haas, Philadelphia, Pa. Other exemplary gelling agents include, cellulosic thickeners, such as derivatized hydroxyethyl cellulose and methyl cellulose, starch-based thickeners, such as acetylated starch, and naturally occurring gums, such as agar, algin, gum arabic, guar gum and xanthan gum. Thickeners and rheology modifiers may also include without limitation acrylates/steareth-20 itaconate copolymer, acrylates/ceteth-20 itaconate copolymer, potato starch modified, hydroxypropyl starch phosphate, acrylates/aminoacrylates/C10-30 alkyl PEG-20 itaconate copolymer, carbomer, acrylates/C10-30 alkyl acrylate crosspolymer, hydroxypropylcellulose, hydroxyethylcellulose, sodium carboxymethylcellulose, polyacrylamide (and) C13-14 isoparaffin (and) laureth-7, acrylamides copolymer (and) mineral oil (and) C13-14 isoparaffin (and) polysorbate 85, hydroxyethylacrylate/sodium acrylol dimethyltaurate copolymer, and hydroxyethylacrylate/sodium acrylol dimethyltaurate copolymer.

In an embodiment of the invention, the cosmetic and personal care composition is a hair cosmetic composition. Optional conventional additives may also be incorporated into the hair cosmetic compositions of this invention to provide certain modifying properties to the composition. Included among these additives are silicones and silicone derivatives; humectants; moisturizers; plasticizers, such as glycerine, glycol and phthalate esters and ethers; emollients, lubricants and penetrants, such as lanolin compounds; fragrances and perfumes; UV absorbers; dyes, pigments and other colorants; anticorrosion agents; antioxidants; detackifying agents; combing aids and conditioning agents; antistatic agents; neutralizers; glossifiers; preservatives; proteins, protein derivatives and amino acids; vitamins; emulsifiers; surfactants; viscosity modifiers, thickeners and rheology modifiers; gelling agents; opacifiers; stabilizers; sequestering agents; chelating agents; pearling agents; aesthetic enhancers; fatty acids, fatty alcohols and triglycerides; botanical extracts; film formers; and clarifying agents. These additives are present in small, effective amounts to accomplish their function, and generally will comprise from about 0.01 to about 10% by weight each, and from about 0.01 to about 20% by weight total, based on the weight of the composition.

The hair cosmetic composition may optionally be a mousse. For mousses, the solvent may be a lower ($C_{1-4}$) alcohol, particularly methanol, ethanol, propanol, isopropanol, or butanol, although any solvent known in the art may be used.

Optionally, an embodiment of the invention may also comprise a spray. For sprays propellants include any optional propellant(s). Such propellants include, without limitation, ethers, such as dimethyl ether; one or more lower boiling hydrocarbons such as $C_3$-$C_6$ straight and branched chain hydrocarbons, for example, propane, butane, and isobutane; halogenated hydrocarbons, such as, hydrofluorocarbons, for example, 1,1-difluoroethane and 1,1,1,2-tetrafluoroethane, present as a liquefied gas; and the compressed gases, for example, nitrogen, air and carbon dioxide.

In yet another aspect, the invention relates to a method of preparing a graft dendrite copolymer composition. The method of preparing the graft dendrite copolymer composition comprises reacting at least one first monomer with a solution of a natural hydroxyl containing component. Then, upon completion of the polymerization of the first monomer, the second monomer is added and this second monomer is polymerized in the presence of the same natural hydroxyl containing component.

The process to produce the graft dendrite copolymers requires that the monomers be added sequentially to the reaction. The natural hydroxyl containing component may be added to the reaction along with the first monomer or may be added to the initial charge. Depending on the application, the relative order of the monomers may be important. For example, if two monomers A and B are used, it may be better to add monomer A before monomer B to the reaction mixture. Additionally, it is within the scope of the invention to add monomer A and then add monomer B and switch back to monomer A and so on. Also, the monomer addition may determine if the product is a solution or a gel. In most cases, the solution is preferred and this will determine the right sequence of monomer addition.

One skilled in the art will recognize that the composition and the properties of the graft dendrite copolymers can be controlled by the sequence of the monomer feed, the relative ratio of the two or more monomers and the initiator system to monomer concentration during each feed. This will control the number of synthetic chains and the length of these synthetic chains attached to the natural hydroxyl containing component. The higher the ratio of initiator to monomer the shorter the attached synthetic chains are. Also, the higher the ratio of initiator to monomer the greater number of the synthetic chains formed. Hence, depending on the application, one may want longer synthetic chains of one of the monomers and shorter synthetic chains of the other monomer attached to the natural hydroxyl containing component. This can be controlled by adjusting the monomer to initiator concentration during the polymerization of each of the monomers. This also changes the number of synthetic chains of each monomer attached to the natural hydroxyl containing component.

In still yet another aspect, the invention relates to a graft dendrite copolymer composition containing both anionic and cationic groups, thus rendering the graft dendrite copolymer composition amphoteric. The anionic moieties can be on the natural hydroxyl containing component with the cationic moieties on the synthetic component or the cationic moieties can be on the natural hydroxyl containing component with the anionic moieties on the synthetic component or combinations thereof. When the natural hydroxyl containing component is a polysaccharide, the anionic material can be an oxidized starch and the cationic moiety can be derived from cationic ethylenically unsaturated monomers such as diallyldimethylammonium chloride. Alternatively, the oxidized starch itself may first be reacted with cationic substituent such as 3-chloro-2-hydroxypropyl) trimethylammonium chloride and then reacted with a synthetic anionic or cationic monomer or mixtures thereof. In another embodiment, a cationic starch may be reacted with an anionic monomer. Finally, the cationic and anionic moieties may be on the synthetic component of these polymers in which case one monomer would be anionic and the other monomer would be cationic. These amphoteric graft dendrite copolymers are particularly useful in hard surface cleaning applications. It is understood that these polymers will contain both a natural hydroxyl containing component and a synthetic component. The cationic moieties are preferably present in the range of 0.001 to 40 mole % of the anionic moieties, more preferably the cationic moieties are present in the range of 0.01 to 20 mole % of the anionic moieties, and most preferably the cationic moieties are present in the range of 0.1 to 10 mole % of the anionic moieties.

EXAMPLES

The following examples are intended to exemplify the present invention but are not intended to limit the scope of the invention in any way. The breadth and scope of the invention are to be limited solely by the claims appended hereto.

Example 1

Example of a using an anionic and a hydrophobic monomer to produce graft dendrite copolymer composition by chain transfer on to a polysaccharide moiety. Copolymer of acrylic acid and methylmethacrylate with acrylic acid aims synthesized before the methylmethacrylate arms using traditional grafting system of Fe(II) and hydrogen peroxide.

A reactor containing 100 grams of water and 38 grams of Cargill MD 01918 (DE 18) and 0.0025 grams of Copper sulfate $5H_2O$ was heated to 98° C. 62.5 grams of acrylic acid was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for 15 minutes. 24 grams of methylmethacrylate was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for an additional hour. The polymer was then neutralized by adding 31 grams of a 50% solution of NaOH. The final product was a thick opaque white solution.

Example 2

Example of a graft dendrite copolymer composition using an anionic and non-ionic monomer. Copolymer of acrylic acid and N,N dimethylacrylamide with acrylic acid arms synthesized before the N,N dimethylacrylamide arms.

A reactor containing 100 grams of water and 38 grams of Cargill MD 01918 (DE 18) and 0.0025 grams of copper sulfate $5H_2O$ was heated to 98° C. 62.5 grams of acrylic acid was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for 30 minutes. The reaction product was partially neutralized using 31 grams of 50% NaOH solution. 24 grams of N,N dimethylacrylamide was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for an additional hour. The final product was an opaque yellow solution.

Example 3

Example of a copolymer with graft dendrite copolymers using an anionic and a amine monomer. Copolymer of acrylic acid and dimethylaminoethyl methacrylate with acrylic acid arms synthesized before the dimethylaminoethyl methacrylate arms.

A reactor containing 100 grams of water and 38 grams of Cargill MD 01918 (DE 18) and 0.0025 grams of copper sulfate $5H_2O$ was heated to 98° C. 62.5 grams of acrylic acid was added to the reactor over a period of 30 minutes. An initiator solution of 7 grams of a 35% solution of hydrogen peroxide in 40 grams of deionized water was simultaneously added to the reactor over a period of 15 minutes. The reaction product was held at 98° C. for 30 minutes. 37.7 grams of dimethylaminoethyl methacrylate was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for an additional hour. The final product was an opaque white solution.

Example 4

Example of a copolymer with graft dendrite copolymers using two non-ionic monomers. Copolymer of acrylamide and hydroxypropyl methacrylate.

A reactor containing 100 grams of water and 38 grams of Cargill MD 01918 (DE 18) and 0.0025 grams of copper sulfate $5H_2O$ was heated to 98° C. 129 grams of hydroxypropyl methacrylate was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for 15 minutes. 34 grams of a 50% solution of acrylamide was added to the reactor over a period of 30 minutes. An initiator solution of 7 grams of a 35% solution of hydrogen peroxide in 40 grams of deionized water was simultaneously added to the reactor over a period of 30 minutes. The reaction product was held at 98° C. for an additional hour. The final product was an opaque white solution.

Example 5

Handwash Fabric Detergent

| Ingredients | wt % |
| --- | --- |
| Linear alkyl benzene sulfonate | 15-30 |
| Nonionic surfactant | 0-3 |
| Na tripolyphosphate (STPP) | 3-20 |
| Na silicate | 5-10 |
| Na sulfate | 20-50 |
| Bentonite clay/calcite | 0-15 |
| Polymer of Example 1 | 1-10 |
| Water | Balance |

Example 6

Liquid Detergent Formulation

| Ingredients | wt % |
| --- | --- |
| Linear alkyl benzene sulfonate | 10 |
| Alkyl sulfate | 4 |
| Alcohol ($C_{12}$-$C_{15}$) ethoxylate | 12 |
| Fatty acid | 10 |
| Oleic acid | 4 |
| Citric acid | 1 |
| NaOH | 3.4 |
| Propanediol | 1.5 |
| Ethanol | 5 |
| Polymer of Example 1 | 1 |
| Ethanol oxidase | 5 u/ml |
| Water, perfume, minors | up to 100 |

Example 7

Personal Care Formulation

Water Repellant Sunscreen

| Ingredients | wt % |
| --- | --- |
| Glycerin | 5.0 |
| Polymer of Example 1 | 2.0 |
| PEG 100 stearate | 5.0 |
| Isostearyl stearate | 4.0 |
| Octyl methoxycinnamate | 7.5 |
| Butyl methoxydibenzoylmethane | 1.5 |
| Hexyl methicone | 5.0 |
| DI water | 70.0 |

Example 8

Personal Care Formulation

Water Repellant Sunscreen

| Ingredients | wt % |
| --- | --- |
| Glycerin | 5.0 |
| Polymer of Example 1 | 2.0 |
| PEG 100 stearate | 5.0 |
| Isostearyl stearate | 4.0 |
| Octyl methoxycinnamate | 7.5 |
| Butyl methoxydibenzoylmethane | 1.5 |
| Hexyl methicone | 5.0 |
| DI water | 70.0 |

Example 9

A reactor containing 100 grams of water and 38 grams of Cargill MD 01918 (DE 18) and 0.003 grams of ferrous ammonium sulfate hexahydrate was heated to 98° C. 99.5 grams of 2-acrylamido-2-methylpropane sulfonate (50% aqueous solution) was added to the reactor over a period of 30 minutes. An initiator solution of 5 grams of a 35% hydrogen peroxide in 40 grams of water was simultaneously added to the reactor over a period of 30 minutes. The reaction product was held at 98° C. for 15 minutes. 62 grams of acrylic acid was added to the reactor over a period of 30 minutes. An initiator solution of 5 grams of a 35% solution of hydrogen peroxide in 40 grams of water was simultaneously added to the reactor over a period of 30 minutes. The reaction product was held at 98° C. for an additional hour. The polymer was then neutralized by adding 6 grams of a 50% solution of NaOH. The final product was a viscous opaque solution with a solids content of 38.6%.

Example 10

A reactor containing 100 grams of water and 38 grams of Cargill MD 01918 (DE 18) and 0.003 grams of ferrous ammonium sulfate hexahydrate was heated to 98° C. 62.5 grams of acrylic acid was added to the reactor over a period of 30 minutes. An initiator solution of 5 grams of a 35% hydrogen peroxide in 40 grams of water was simultaneously added to the reactor over a period of 30 minutes. The reaction product was held at 98° C. for 15 minutes. 99.5 grams of 2-acrylamido-2-methylpropane sulfonate (50% aqueous solution) was added to the reactor over a period of 30 minutes An initiator solution of 5 grams of a 35% solution of hydrogen peroxide in 40 grams of water was simultaneously added to the reactor over a period of 30 minutes. The reaction product was held at 98° C. for an additional hour. The polymer was then neutralized by adding 6 grams of a 50% solution of NaOH. The final product was a viscous opaque solution with a solids content of 38.5%.

Example 11

Example of a graft dendrite copolymer composition using acrylic acid and itaconic acid: Copolymer of acrylic acid and itaconic acid with acrylic acid arms synthesized before the itaconic acid arms.

A reactor containing 145.5 grams of water and 158 grams of Star DRI 100 (95% DE 18 powder maltodextrin from Tate and Lyle) was heated to 85° C. 0.0082 gms of ferrous ammonium sulfate hexahydrate in 5.0 grams of water was added to the reactor. The solution was light milky in color. 25 grams of acrylic acid in 25 grams of water was added to the reactor over a period of 50 minutes. An initiator solution of 10 grams of 35% hydrogen peroxide in 10 grams of water was simultaneously added to the reactor over a period of 60 minutes. The solution changed into a light yellow color after initial addition of acrylic acid. The reaction product was held at 85° C. for 30 minutes. The residual acrylic acid content was 3400 ppm which indicates that about 5.1% of the initial acrylic acid was unreacted. 25 grams of itaconic acid reacted with 15.4 grams of 50% sodium hydroxide dissolved in 40 grams of water was added to the reactor over a period of 50 minutes. An initiator solution of 10 grams of 35% hydrogen peroxide in 20 grams of water was simultaneously added to the reactor over a period of 60 minutes. The reaction product was held at 85° C. for an additional hour. The final product was a clear light yellow solution with the solid concentration of 42%.

Example 12

Example of a graft dendrite copolymer composition using acrylic acid and methacrylic acid: Copolymer of acrylic acid and methacrylic acid with acrylic acid arms synthesized before the methacrylic acid arms.

A reactor containing 165 grams of water and 168 grams of Star DRI 180 (95% DE 18 powdered dent maltodextrin from Tate and Lyle) was heated to 85° C. 0.01 grams of ferrous ammonium sulfate hexahydrate in 5.0 grams of water was added to the reactor. The solution was light milky color. 20 grams of acrylic acid in 25 grams of water was added to the reactor over a period of 50 minutes. An initiator solution of 10 grams of 35% hydrogen peroxide in 10 grams of water was simultaneously added to the reactor over a period of 60 minutes. The solution changed into a light yellow color after initial addition of acrylic acid. The reaction product was held at 85° C. for 30 minutes. The residual acrylic acid content was 300 ppm which indicates that about 0.6% of the initial acrylic acid was unreacted. 20 grams of methacrylic acid in 25 grams of water was added to the reactor over a period of 50 minutes. An initiator solution of 10 grams of 35% hydrogen peroxide in 20 grams of water was simultaneously added to the reactor over a period of 60 minutes. The reaction product was held at 85° C. for an additional hour. The final product was slightly opaque water white viscous polymer solution with the solid concentration of 42%.

Example 13

Example of a graft dendrite copolymer composition using acrylic acid and diallyldimethylammonium chloride (DADMAC): Copolymer of acrylic acid and DADMAC with acrylic acid arms synthesized before the DADMAC aims.

A reactor containing 145.5 grams of water and 158 grams of Star DRI 100 (95% DE 18 powdered dent maltodextrin from Tate and Lyle) was heated to 85° C. 0.0082 gms of ferrous ammonium sulfate hexahydrate in 5.0 grams of water was added to the reactor. The solution was light milky white in color. 25 grams of acrylic acid in 25 grams of water was added to the reactor over a period of 50 minutes. An initiator solution of 10 grams of 35% hydrogen peroxide in 10 grams of water was simultaneously added to the reactor over a period of 60 minutes. The solution changed into a light yellow color after initial addition of acrylic acid. The reaction product was held at 85° C. for 30 minutes. The reaction product was neutralized with 23.7 grams of 50% sodium hydroxide. The residual acrylic acid level was 3840 ppm which indicates that 5.8% of the acrylic acid was unreacted. 38.46 grams of 65% solution of DADMAC in 40 grams of water was added to the reactor over a period of 50 minutes. An initiator solution of 10 grams of 35% hydrogen peroxide in 20 grams of water was simultaneously added to the reactor over a period of 60 minutes. The solution changed to a clear water white color over the period of addition of DADMAC with a lot of bubbles in the reaction product. The reaction product was held at 85° C. for an additional hour. The final product was clear water white polymer solution with the solid concentration of 41%.

Example 14

Example of a graft dendrite copolymer composition using acrylic acid and dimethylaminoethyl methacrylate, methyl chloride quaternary:

A reactor containing 145.5 grams of water and 126 grams of Star DRI 100 (95% DE 18 powdered dent maltodextrin from Tate and Lyle) was heated to 85° C. 0.0082 gms of ferrous ammonium sulfate in 5.0 grams of water was added to the reactor. 40 grams of acrylic acid in 25 grams of water was added to the reactor over a period of 50 minutes. An initiator solution of 10 grams of 35% hydrogen peroxide in 10 grams of water was simultaneously added to the reactor over a period of 60 minutes. The solution changed into a light yellow color after initial addition of acrylic acid. The reaction product was held at 85° C. for 30 minutes. The product was neutralized with 30.8 grams of 50% sodium hydroxide. The residual acrylic acid level was 4140 ppm which indicates that about 3.7% of the initial acrylic acid was unreacted. 50 grams of dimethylaminoethyl methacrylate, methyl chloride quaternary (80% solution) in 40 grams of water was added to the reactor over a period of 50 minutes. An initiator solution of 10 grams of 35% hydrogen peroxide in 20 grams of water was simultaneously added to the reactor over a period of 60 minutes. The reaction product was held at 85° C. for an additional hour. The final product was slightly opaque water white polymer solution with the solid concentration of 40%.

Example 15

A reactor containing 150.5 grams of water, 178.7 grams of Staley 1300 (82% DE 42 corn syrup from Tate and Lyle), 19.4 grams of maleic anhydride and 16.1 grams of 50% NaOH was heated to 85° C. 0.0082 gms of ferrous ammonium sulfate hexahydrate in 5.0 grams of water was added to the reactor. The solution was light yellow in color. 29 grams of acrylic acid in 70 grams of water was added to the reactor over a period of 120 minutes. An initiator solution of 30 grams of 35% hydrogen peroxide in 10 grams of water was simultaneously added to the reactor over a period of 120 minutes. The solution turned amber in color during this time. The reaction product was held at 95° C. for 30 minutes. The solution changed to light yellow color during this time. The residual acrylic acid content was 181 ppm which indicates that about 0.29% of the initial acrylic acid was unreacted. The residual maleic acid content was 68 ppm which indicates that about 0.14% of the initial maleic acid was unreacted. 20 grams of a 50% solution of sodium 2-acrylamido-2-methylpropane sulfonate dissolved in 20 grams of water was added to the reactor over a period of 30 minutes. An initiator solution of 10 grams of 35% hydrogen peroxide in 20 grams of water was simultaneously added to the reactor over a period of 30 minutes. The reaction product was held at 95° C. for an additional hour. The final product was a clear yellow solution with the solid concentration of 36%.

Comparative Example 1

A reactor containing 145.5 grams of water, 178.7 grams of Staley 1300 (82% DE 42 corn syrup from Tate and Lyle), 19.4 grams of maleic anhydride and 16.1 grams of 50% NaOH was heated to 95° C. 0.0082 gms of ferrous ammonium sulfate hexahydrate in 5.0 grams of water was added to the reactor. The solution was light yellow in color. 29 grams of acrylic acid in and 20 grams of a 50% solution of sodium 2-acrylamido-2-methylpropane sulfonate dissolved in 70 grams of water was added to the reactor over a period of 120 minutes. An initiator solution of 30 grams of 35% hydrogen peroxide in 10 grams of water was simultaneously added to the reactor over a period of 120 minutes. The solution turned amber in color during this time. The reaction product was held at 95° C. for 60 minutes. The final product was a clear yellow solution with solids of 37%.

Example 16

The polymer solutions from Example 15 and Comparative Example 1 were evaluated in a dispersancy test below:
1. For each dispersancy test, solutions A and B were prepared
    A. One percent polymer solution
    B. Test solution: 98 grams DI water, 2 grams Bradley Brown clay, dispersed for 20 minutes (250 rpm with stir rod)
2. 40 μL of A was dosed into B (1:5000 polymer:clay).
3. The solutions were stirred for an additional minute
4. The solutions were then poured into 100 mL graduated cylinder.
5. The amount and rate of settling across samples were compared.
In the FIGURE, Left: solution using polymer of example 15, Right: solution using polymer of Comparative Example 1. The picture in the FIGURE was taken 20 minutes into the test. The picture indicates that the graft dendrite polymer of Example 15 of the present invention is far superior as a dispersant to the polymer of Comparative Example 1.

Example 17

104 grams a lignosulfonate solution (ARBO S08 50% solution available from Tembec Chemical Products Group) was mixed with 25 grams of water and 0.003 grams of ferrous ammonium sulfate hexahydrate and heated to 94° C. A monomer solution containing 30 grams of acrylic acid was added for 60 minutes. Simultaneously an initiator solution comprising of 2 grams of a 35% hydrogen peroxide solution in 30 grams of water was added to the reactor at the same time as the monomer solution over a period of 70 minutes. The resulting product was held at 94° C. for 30 minutes. Next 40 grams of a 50% solution of Na 2-acrylamido-2-methyl propane sulfonate and 38 grams of water was subsequently added to the reactor over a period of 60 minutes. An initiator solution comprising of 1.4 grams of a 35% hydrogen peroxide solution in 30 grams of water was added to the reactor at the same time as the monomer solution over a period of 70 minutes. The reaction product was held at 94° C. for an additional 60 minutes. The final product was a dark amber/black colored solution.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

The invention claimed is:

1. A copolymer obtained by the polymerization of at least one first ethylenically unsaturated monomer and at least one second ethylenically unsaturated monomer that is different from said first ethylenically unsaturated monomer, in the presence of a natural hydroxyl containing component selected from the group consisting of small natural alcohols, monosaccharides, disaccharides, oligosaccharides, polysaccharides and combination thereof, wherein said small natural alcohols are selected from the group consisting of glycerol, citric acid, lactic acid, tartaric acid, gluconic acid, ascorbic acid, and glucoheptonic acid, the polymerization being initiated by a metal ion catalyst and said first and said second ethylenically unsaturated monomers are polymerized sequentially, wherein the at least one first and the at least one second ethylenically unsaturated monomers are attached at different points on the natural hydroxyl containing component and wherein the copolymer is water soluble, with the proviso that when at least one of the first and the second ethylenically unsaturated monomer is cationic, the polymerization is performed substantially in the absence of a crosslinking agent.

2. The copolymer of claim 1 wherein the at least one first ethylenically unsaturated monomer is anionic.

3. The copolymer of claim 1 wherein the at least one first ethylenically unsaturated monomer is selected from the group consisting of acrylic acid, methacrylic acid, ethacrylic acid, α-chloro-acrylic acid, α-cyano acrylic acid, β-methylacrylic acid (crotonic acid), α-phenyl acrylic acid, β-acryloxy propionic acid, sorbic acid, α-chloro sorbic acid, angelic acid, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, 2-acrylamido-2-methyl propane sulfonic acid and its sodium salt (AMPS), vinyl sulfonic acid, sodium methallyl sulfonate, sulfonated styrene, (meth)allyloxybenzene sulfonic acid, vinyl phosphonic acid, sodium 1-allyloxy 2 hydroxy propyl sulfonate and maleic acid and their salts.

4. The copolymer of claim 1 wherein the at least one second ethylenically unsaturated monomer is anionic.

5. The copolymer of claim 1 wherein the at least one second ethylenically unsaturated monomer is selected from the group consisting of acrylic acid, methacrylic acid, ethacrylic acid, α-chloro-acrylic acid, α-cyano acrylic acid, β-methyl-acrylic acid (crotonic acid), α-phenyl acrylic acid, β-acryloxy propionic acid, sorbic acid, α-chloro sorbic acid, angelic acid, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, 2-acrylamido-2-methyl propane sulfonic acid and its sodium salt (AMPS), vinyl sulfonic acid, sodium methallyl sulfonate, sulfonated styrene, (meth)allyloxybenzene sulfonic acid, vinyl phosphonic acid, sodium 1-allyloxy 2 hydroxy propyl sulfonate and maleic acid and their salts.

6. The copolymer of claim 1 wherein the at least one first ethylenically unsaturated monomer is non-anionic.

7. The copolymer of claim 1 wherein the at least one second ethylenically unsaturated monomer is non-anionic.

8. The copolymer of claim 1, wherein the at least one first ethylenically unsaturated monomer is anionic and the at least one second ethylenically unsaturated monomer is non-anionic.

9. The copolymer of claim 1, wherein the at least one second ethylenically unsaturated monomer is anionic and the at least one first ethylenically unsaturated monomer is non-anionic.

10. The copolymer of claim 1, wherein the copolymer is anionic, cationic, zwitterionic, ionic or amphoteric.

11. The copolymer of claim 1 wherein the natural hydroxyl containing component is a polysaccharide.

12. The copolymer composition of claim 1 wherein the polysaccharides are selected from the group consisting of chitin, chitosan, gum arabic, agar, algin, carrageenan, xanthan, gellan, welan, rhamsan, curdlan scleroglucan, tamarind gum, hemicelluloses, cellulose, d-xylans, maltodextrin, corn syrup, starch, combinations thereof and derivatives thereof.

13. The copolymer of claim 1 having the structure:

wherein m is the average number of repeat units of the first ethylenically unsaturated monomer; m is the average number of repeat units of the second ethylenically unsaturated monomer; K is the moiety derived from the first ethylenically unsaturated synthetic monomer; L is the moiety derived from the second ethylenically unsaturated synthetic monomer.

14. The copolymer of claim 1 wherein the first ethylenically unsaturated monomer is anionic and is selected from the group consisting of acrylic acid, itaconic acid, maleic acid, methacrylic acid, 2-acrylamido-2-methyl propane sulfonic acid and their salts and combinations thereof, and the second ethylenically unsaturated monomer is cationic and is selected from the group consisting of methacrylamidopropyltrimethyl ammonium chloride (MAPTAC), diallyldimethyl ammonium chloride (DADMAC), acryloyloxyethyl trimethyl ammonium chloride (AETAC), methacryloyloxyethyl trimethyl ammonium chloride and combinations thereof.

15. A process for preparing a copolymer comprising polymerizing at least one first one ethylenically unsaturated monomer and at least one second ethylenically unsaturated monomer that is different from the first ethylenically unsaturated monomer, in the presence of a natural hydroxyl containing component selected from the group consisting of small natural alcohols, monosaccharides, disaccharides, oligosaccharides, polysaccharides and combination thereof, wherein said small natural alcohols are selected from the group consisting of glycerol, citric acid, lactic acid, tartaric acid, gluconic acid, ascorbic acid, and glucoheptonic acid, wherein the monomers are polymerized sequentially, wherein the polymerization is metal ion catalyst initiated and wherein the copolymer is water soluble, wherein the at least one first and the at least one second ethylenically unsaturated monomers are attached at different points on the natural hydroxyl containing component, with the proviso that if at least one of the first and the second ethylenically unsaturated monomers is cationic, said polymerization is performed in the substantial absence of a cross-linking agent.

16. The copolymer of claim 1 wherein the at least one first ethylenically unsaturated monomer is cationic or nonionic.

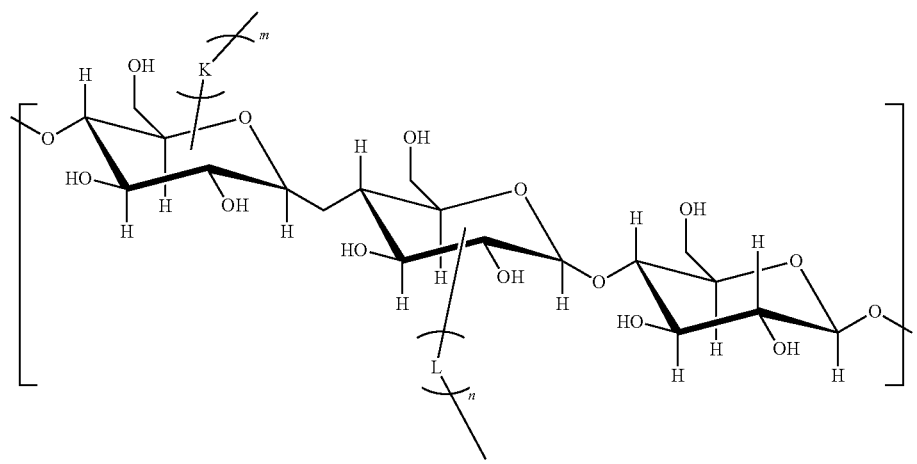

17. The copolymer of claim 1 wherein the at least one second ethylenically unsaturated monomer is cationic or nonionic.

18. The copolymer of claim 1 wherein the polysaccharide is maltodextrin, corn syrup or starch.

* * * * *